United States Patent [19]

Anisimova et al.

[11] Patent Number: 5,623,073
[45] Date of Patent: Apr. 22, 1997

[54] BENZIMIDAZOLE COMPOUNDS

[75] Inventors: Vera A. Anisimova; Margarita V. Levchenko; Tatyana B. Korochina, all of Rostov-On-Don; Alexander A. Spasov, Volgograd; Sergei G. Kovalev, Volgograd; Galina P. Dudchenko, Volgograd, all of Russian Federation

[73] Assignee: Adir Et Compagnie, Courbevoie, France

[21] Appl. No.: 63,531

[22] Filed: May 18, 1993

[30] Foreign Application Priority Data

May 19, 1992 [FR] France .................. 92 06036
Jul. 31, 1992 [FR] France .................. 92 09488

[51] Int. Cl.$^6$ ............... C07D 471/02; C07D 239/70
[52] U.S. Cl. ................. 544/252; 544/250
[58] Field of Search ............... 544/252, 250; 514/393, 394, 395

[56] References Cited

U.S. PATENT DOCUMENTS 5,008,282  4/1991  Tomiyama et al. .............. 548/320.1

FOREIGN PATENT DOCUMENTS 2131330  1/1972  Germany .

OTHER PUBLICATIONS

Anisimova et al., "Synthesis and pharmacological activity of some 2,3-dihydroimidazo[1,2-a]binzimidazoles and their intermediates", Khim.-Farm. Zh., 21(3), 313–319, 1987.

Abstract, "Synthesis and pharmacological activity of N-substituted 1-aminoethyl-2,3-dihydroimidazo [1,2-a] benzimidazoles", Anisimova et al., Khim–Farm. Zh. 22(10) pp. 1212–1217 (1988).

Abstract, "Substituted 1,2,3,4-tetrahydropyrimido [1,2-a] benzimidazoles with central nervous system activity", European J. Med. Chem.–Chim. Ther. (1981), 16(11), pp. 327–332.

Primary Examiner—Gary Geist
Assistant Examiner—Dwayne C. Jones
Attorney, Agent, or Firm—The Firm of Gordon W. Hueschen

[57] ABSTRACT

Compounds of the general formula (I):

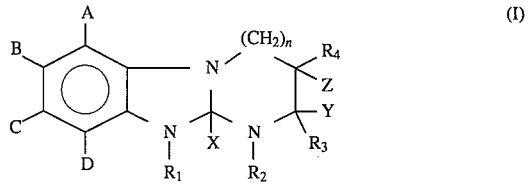

wherein A, B, C, D, n, $R_1$, $R_2$, $R_3$, $R_4$, X, Y and Z are as defined in the description, and their use as antidiabetics are disclosed.

12 Claims, No Drawings

BENZIMIDAZOLE COMPOUNDS

The present invention relates to new tricyclic benzimidazole compounds, a process for their preparation, and pharmaceutical compositions containing them.

Imidazo[1,2-a]benzimidazoles possessing antihypertensive properties and central nervous system-depressant properties are known (Khim Farm., Zh 79, 13, (8) pp 57–62).

The Applicant has now discovered tricyclic benzimidazole compounds that exhibit an antidiabetic activity and at the same time a significant platelet anti-aggregation activity. The combination of antidiabetic and platelet anti-aggregation activities in one and the same molecule is at present novel and is of particular interest therapeutically. It is known by the person skilled in the art that, apart from the metabolic problems associated with diabetes, the prognosis of that disease is aggravated by a significant risk of vascular complications (Goodman and Gilman's—The pharmacological basis of Therapeutics, 8th edition, p. 1471). Those complications require substantial monitoring and separate treatment. As a result of their platelet anti-aggregation activity, currently not known in compounds having an antidiabetic activity, the compounds of the invention, whilst treating the metabolic disorders causing diabetes, also have a preventative and curative effect on cardiovascular disorders that are an inevitable consequence of that disease. Based on that alone, the compounds of the invention represent decisive progress in the treatment of diabetes compared with all the antidiabetic agents known in the art. Finally, it is important to point out that the compounds of the present invention do not have any effect on arterial pressure, contrary to what might be expected from the β-phenylethylamine structure of certain compounds of the invention as well as from results of the prior art already mentioned.

The present invention relates more especially to compounds of the general formula (I):

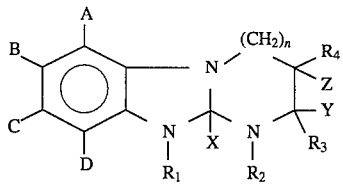

(I)

wherein:
either:
1.
n=0
A, B, C and D, which are the same or different, each represents hydrogen, halogen, a lower alkyl group, a lower alkoxy group, a hydroxy group, a trifluoromethyl group or a hydroxy-lower alkyl group,
Y and Z each represents hydrogen or together form a bond, and either:
1.A.
X and $R_2$ together form a bond and in that case:
1.A.1
$R_1$ represents a $G_1$ group,
$G_1$ represents the group

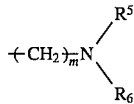

in which m is an integer of from 1 to 6 inclusive and $R_5$ and $R_6$, which are the same or different:
a/ each represents, independently of the other, hydrogen, a lower alkyl group, an aryl-lower alkyl group or a substituted aryl-lower alkyl group, and $R_3$ represents hydrogen, a lower alkyl group, a phenyl nucleus substituted by a lower alkyl group, by a hydroxy or hydroxyalkyl group or by from two to five groups selected from lower alkyl, lower alkoxy, halogen, trifluoromethyl, hydroxy and hydroxyalkyl, or $R_3$ represents a naphthyl nucleus, a substituted naphthyl nucleus, a heteroaryl group, a substituted heteroaryl group, or a group $G_1$, $G_1$ being as defined hereinbefore, b/ or $R_5$ and $R_6$ together with the nitrogen atom that carries them form a morpholine system, and $R_3$ represents hydrogen, a lower alkyl group, a phenyl nucleus substituted by a lower alkyl group, hydroxy, halogen, trifluoromethyl or by hydroxyalkyl, or by from two to five groups selected from lower alkyl, lower alkoxy, halogen, trifluoromethyl, hydroxy and hydroxyalkyl, or $R_3$ represents a naphthyl nucleus, a substituted naphthyl nucleus, a heteroaryl group, a substituted heteroaryl group, or a group $G_1$, $G_1$ being as defined herein before, c/ or $R_5$ and $R_6$ together with the nitrogen atom that carries them form a piperidine, pyrrolidine or piperazine system each of which is optionally substituted at the nitrogen atom in the 4-position by a lower alkyl group, an aryl group, an aryl-lower alkyl group, a substituted aryl group or a substituted aryl-lower alkyl group, and $R_3$ represents a lower alkyl group, a phenyl nucleus substituted by hydroxy, halogen, trifluoromethyl or by a hydroxyalkyl group or by from two to five groups selected from lower alkyl, lower alkoxy, halogen, trifluoromethyl, hydroxy and hydroxyalkyl, or $R_3$ represents a naphthyl nucleus, a substituted naphthyl nucleus, a heteroaryl group or a substituted heteroaryl group; or $R_1$ represents a group $G_2$, $G_2$ denoting a $(CH_2)_mCOR_7$ group, or $G_3$, $G_3$ denoting a $(CH_2)_mCHOHR_7$ group, wherein m is as defined hereinbefore and $R_7$ represents an aryl group or a substituted aryl group, and $R_3$ represents hydrogen, a lower alkyl group, a phenyl nucleus substituted by hydroxy, a hydroxyalkyl group, a lower alkoxy group or by a lower alkyl group or by from two to five groups selected from lower alkyl, lower alkoxy, halogen, trifluoromethyl, hydroxy and hydroxyalkyl, or $R_3$ represents a naphthyl nucleus, a substituted naphthyl nucleus, a heteroaryl group, a substituted heteroaryl group, or a group $G_1$, $G_1$ being as defined hereinbefore, $R_4$ represents hydrogen, a group $G_1$ with $G_1$ being as defined hereinbefore, a group $G_4$, that is to say a group of the formula:

—COO—$G_1$ wherein $G_1$ is as defined hereinbefore, or a group $G_5$, that is to say $COR_9$, wherein $R_9$ represents an aryl group, a substituted aryl group, a heteroaryl group or a substituted heteroaryl group, with the exception of compounds in which $R_4$ represents hydrogen at the same time as $R_1$ represents a group:

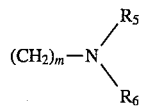

wherein m=2
and $R_5$ and $R_6$ each represents an ethyl group whilst at the same time $R_3$ represents a lower alkyl group or a naphthyl group,
1.A.2
X and $R_2$ together form a bond and $R_1$ represents a group $G_6$, that is to say a group $(CH_2)_mR_8$, m being as defined hereinbefore and $R_8$ representing a lower alkyl group, or representing phenyl or substituted phenyl or naphthyl or substituted naphthyl, and $R_3$ represents a lower alkyl group, an aryl group, a substituted aryl group, a heteroaryl group, a substituted heteroaryl group, hydrogen or a group $G_1$, $G_1$ being as defined hereinbefore, and $R_4$ represents a group $G_1$, $G_4$ or $G_5$, $G_1$, $G_4$ and $G_5$ being as defined hereinbefore, or

1.A.3

X and $R_2$ together form a bond and $R_1$ represents methyl, and $R_3$ represents a lower alkyl group, an aryl group, a substituted aryl group, a heteroaryl group, a substituted heteroaryl group, hydrogen or a group $G_1$, $G_1$ being as defined hereinbefore, and $R_4$ represents a group $G_4$, $G_4$ being as defined hereinbefore, or a group $G_7$, $G_7$ denoting the group $COR_{10}$ wherein $R_{10}$ represents a naphthyl group, a substituted naphthyl group, a substituted phenyl group, a heteroaryl group or a substituted heteroaryl group, or

1.B

X and $R_1$ together form a bond, $R_2$ represents:

a group $G_1$, $G_1$ being as defined hereinbefore, and $R_3$ represents a lower alkyl group, a substituted phenyl group, a naphthyl group, a substituted naphthyl group, a heteroaryl group, a substituted heteroaryl group or a group $G_1$, $G_1$ being as defined hereinbefore, whilst $R_4$ represents a hydrogen atom or a group $G_1$, $G_4$ or $G_5$, $G_4$ and $G_5$ being as defined hereinbefore, or represents a group $G_2$ or a group $G_3$, $G_2$ and $G_3$ being as defined hereinbefore, and $R_3$ represents a hydrogen atom, a lower alkyl group, an aryl group, a substituted aryl group, a heteroaryl group, a substituted heteroaryl group or a group $G_1$, $G_1$ being as defined hereinbefore, whilst $R_4$ represents a hydrogen atom or a group $G_1$, $G_4$ or $G_5$, $G_4$ and $G_5$ being as defined hereinbefore, or

2.

n=1,

A, B, C and D, which are the same or different, each represents a hydrogen atom, a halogen atom, a lower alkyl group or a trifluoromethyl group, X and $R_1$ form a bond or X and $R_2$ form a bond, wherein at least one of those two bonds must be present in the molecule, Y and Z each represents a hydrogen atom or together form a bond, $R_1$ or $R_2$—depending on whether X and $R_2$ or X and $R_1$ form a bond—represents a methyl group or $G_1$ or $G_2$ or $G_3$ or $G_6$, $G_1$, $G_2$, $G_3$ and $G_6$ each being as defined hereinbefore, $R_3$ represents, whatever the meanings of $R_1$ and $R_2$, hydrogen, a lower alkyl group, an aryl group, a substituted aryl group, a heteroaryl group, a substituted heteroaryl group or a group $G_1$, $G_1$ being as defined hereinbefore, and $R_4$ represents a hydrogen atom or a group $G_1$ or $G_4$ or $G_5$, $G_1$, $G_4$ and $G_5$ being as defined hereinbefore, their stereoisomers, as well as their addition salts with a pharmaceutically acceptable acid, there being understood by a lower alkyl or lower alkoxy group a straight-chain or branched group containing from 1 to 6 carbon atoms, there being understood by aryl group a phenyl or naphthyl group, and by heteroaryl group a furyl, thienyl, pyridyl, pyrrolyl, imidazolyl, benzimidazolyl, benzofuryl, benzothienyl, quinolyl, isoquinolyl or indolyl group, the term "substituted" qualifying the terms arylalkyl, aryl, phenyl, naphthyl and heteroaryl indicating, unless specified otherwise, that the groups in question are substituted in the cyclic moiety by from one to three radicals selected from halogen, trifluoromethyl, hydroxy, lower alkoxy, hydroxy-lower alkyl and lower alkyl, and that if there exists in one molecule several $G_1$ groups or $R_5$ and $R_6$ groups, those may be the same or different.

Of the pharmaceutically acceptable acids that may be used to form an addition salt of the compounds of formula (I) there may be mentioned by way of non-limiting example hydrochloric, sulfuric, tartaric, maleic, fumaric, oxalic, ethanesulfonic, camphonic, ethanesulfonic and citric acid etc.

The invention relates also to a process for the preparation of compounds of the general formula (I) which is characterised in that:

A—when a compound of formula (I) is desired wherein X and $R_2$ together form a bond, there is used as starting material a compound of formula (II):

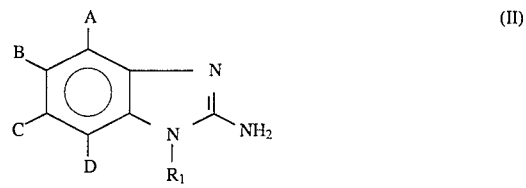

wherein A, B, C. D and $R_1$ are as defined hereinbefore, the compound of formula (II) being obtained as described in the literature (of which there may be cited by way of example and without implying any limitation Tetrahedron 1976, 32(7), 839–842 or Khim Heterosikl, Soedin 1969(5), 869–873).

which is treated:

* when a compound of formula (I) is desired wherein Y and Z each represents a hydrogen atom, with a compound of formula (III/A):

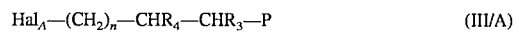

wherein $Hal_A$ represents halogen, n, $R_3$ and $R_4$ are as defined hereinbefore and P represents a leaving group selected from halogen and hydroxy.

to yield a compound of formula (IV/A):

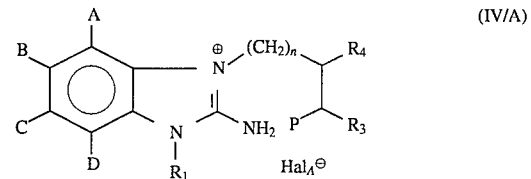

wherein A, B, C, D and $R_1$ are as defined for formula (I) and n, $R_3$, $R_4$ and P are as defined hereinbefore, which by means of heating, preceded, when P represents a hydroxy group, by treatment with a halogenation agent, yields a compound of formula (I/B):

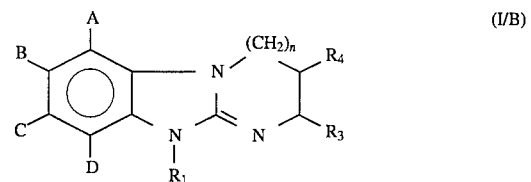

a particular case of compounds of formula (I) wherein A, B, C, D, $R_1$, $R_3$, $R_4$ and n are as defined hereinbefore, X and $R_2$ together forming a bond and Y and Z each representing a hydrogen atom,

* when a compound of formula (I) is desired wherein Y and Z together form a bond,
with a compound of formula (III):

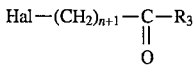  (III)

wherein n is as defined hereinbefore, R₃ is as defined for formula (I) as a function of the meanings of R₁, and Hal represents a halogen atom,
to yield a compound of formula (IV):

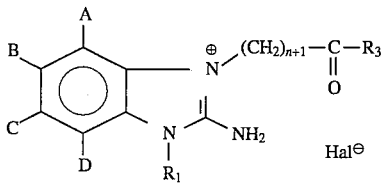  (IV)

wherein Hal, A, B, C, D, R₁, n and R₃ are as defined hereinbefore,
which, by means of heating, yields a compound of formula (I/A):

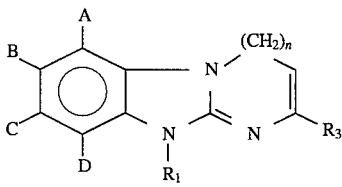  (I/A)

a particular case of compounds of formula (I) wherein A, B, C, D, R₁, R₃ and n are as defined hereinbefore, X and R₂ on the one hand, and Y and Z on the other hand, together form a bond, and R₄ represents hydrogen,
which compound of formula (I/A), when a compound of formula (I) is desired in which R₄ is other than hydrogen, is treated:

when a compound of formula (I) is desired wherein R₄ represents a group G₄ and Y and Z represent a bond, with a compound of formula (V/A):

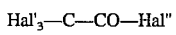  (V/A)

wherein Hal' and Hal", which are the same or different, each represents halogen, to yield a compound of formula (VI):

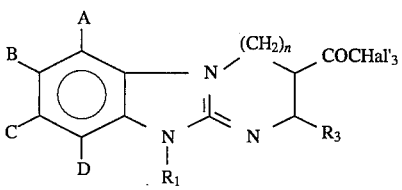  (VI)

wherein A, B, C, D, R₁, n, R₃ and Hal'₃ are as defined hereinbefore,
which compound of formula (VI) is treated with a compound of formula VII:

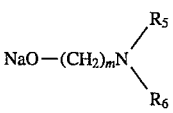  (VII)

wherein m, R₅ and R₆ are as defined for the formula of group G₄ as defined for formula (I), to yield a compound of formula (I/C):

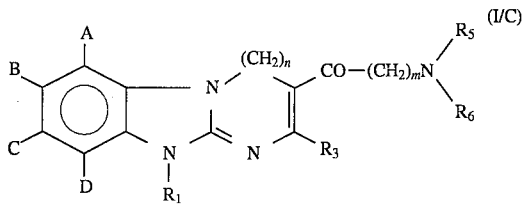  (I/C)

wherein A, B, C, D, R₁, R₃, R₅, R₆ and n are as defined for formula (I),
Y and Z on the one hand, and X and R₂ on the other hand, together forming a double bond, and R₄ representing a group G₄,

* when a compound of formula (I) is desired wherein R₄ represents a group G₄ and Y and Z represent a bond, with a compound of formula (VIII):

  (VIII)

wherein Hal''' and Hal₄, which are the same or different, each represents a halogen atom and m is as defined hereinbefore, to yield a compound of formula (IX):

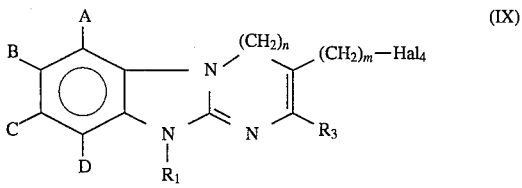  (IX)

wherein A, B, C, D, R₁, n, p, R₃ and Hal₄ are as defined hereinbefore,
which is then treated with a compound of formula (X):

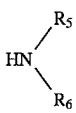  (X)

wherein R₅ and R₆ are as defined hereinbefore,
to yield a compound of formula (I/D):

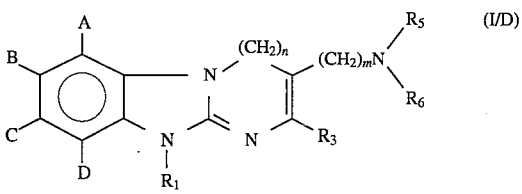  (I/D)

a particular case of compounds of formula (I) wherein A, B, C, D, R₁ and n are as defined for formula (I), and X and R₂ on the one hand, and Y and Z on the other hand, together forming a bond, and R₄ forming a group G₁ as defined for formula (II),

* when a compound of formula (I) is desired wherein R₄ represents a group G₅ or G₇ and Y and Z represent a bond, with a compound of formula (XI):

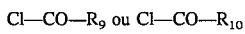  (XI)

depending on the compound desired, R₉ and R₁₀ being as defined hereinbefore, to yield a compound of formula (I/E):

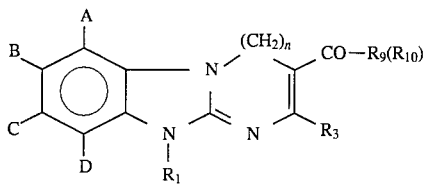

a particular case of compounds of formula (I) wherein A, B, C, D, n and $R_3$ are as defined hereinbefore, X and $R_2$ on the one hand, and Y and Z on the other hand, together forming a bond, and $R_4$ representing a group $G_5$ or $G_7$ as defined hereinbefore, B.
when a compound of formula (I) is desired wherein X and $R_1$ together form a bond,
there is used as starting material a compound of formula (XII):

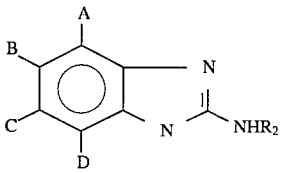

wherein A, B, C, D and $R_2$ are as defined hereinbefore, which

* when a compound of formula (I) is desired wherein Y and Z each represents hydrogen, is treated
with a compound of formula (III/A) as defined hereinbefore to yield, after heating, a compound of formula (I/G):

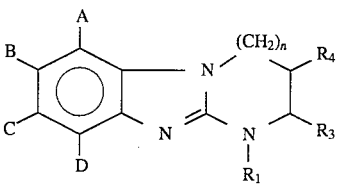

a particular case of compounds of formula (I) wherein A, B, C, D, n, $R_1$, $R_3$ and $R_4$ are as defined hereinbefore, X and $R_1$ together forming a bond and Y and Z each representing a hydrogen atom,

* when a compound of formula (I) is desired wherein Y and Z form a bond, is treated
with a compound of formula (III) as defined hereinbefore, to yield, after heating, a compound of formula (I/F):

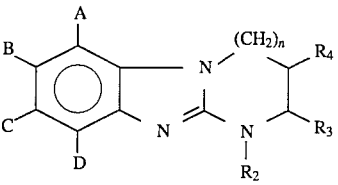

a particular case of compounds of formula (I) wherein A, B, C, D, n, $R_2$ and $R_3$ are as defined hereinbefore, X and $R_1$ on the one hand, and Y and Z on the other hand, together forming a bond, and $R_4$ representing hydrogen, which compound of formula (I/F), depending on the meaning of $R_4$ in the desired compound of formula (I), may be treated:

in succession, as indicated hereinbefore, with a compound of formula (V/A) as defined hereinbefore then with a compound of formula (VII) as defined hereinbefore, in succession, as indicated hereinbefore, with a compound of formula (VIII) as defined hereinbefore then with a compound of formula (X) as defined hereinbefore, or with a compound of formula (XI) as defined hereinbefore, to yield a compound of formula (I/H):

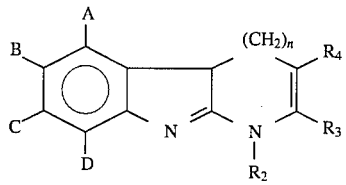

a particular case of compounds of formula (I) wherein A, B, C, D, n, $R_2$, $R_3$ and $R_4$ are as defined for formula (I), X and $R_1$ on the one hand, and Y and Z on the other hand, together forming a bond, which compounds of formulae (I), (I/A), (I/B), (I/C), (I/D), (I/E), (I/F), (I/G), (I/H) are, if necessary, purified by a technique selected from chromatography and/or crystallisation, and, if desired, converted with an acid into pharmaceutically acceptable salts.

The process for the synthesis of compounds of formula (I) indicated above is very general and may be subjected to any modifications that a person skilled in the art might consider appropriate in order to carry out a synthesis specifically designed for any product of formula (I) he might wish to obtain, this obviously being a function of the nature of the substituents A, B, C, D, $R_1$, $R_2$, $R_3$ and $R_4$. A certain number of non-limiting variants are described below.

One of the variants comprises subjecting to reduction with an alkali metal mixed hydride a compound of formula (IV/B):

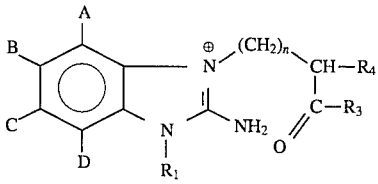

obtained by condensing a compound of formula (II) with a compound of formula (III/B):

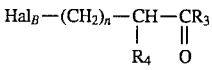

wherein $Hal_B$ represents a halogen atom and n, $R_3$ and $R_4$ are as defined hereinbefore
to yield a compound of formula (IV/A) as defined hereinbefore in which the group P represents a hydroxy group which compound, treated with a halogenation agent and then heated, yields a compound of formula (I/B) as defined hereinbefore.

Another variant relates to obtaining compounds of formula (I/B) as defined hereinbefore in which $R_1$ represents a group $G_2$ or $G_3$, and Y and Z each represents hydrogen.

In that case, there is used as starting material a compound of formula (XIII):

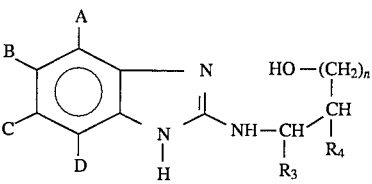

wherein A, B, C, D and n are as defined hereinbefore, which is treated with a halogenation agent and then by heating to yield a compound of formula (XIV):

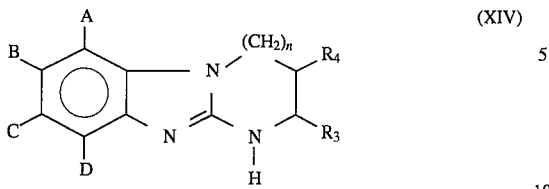
(XIV)

wherein A, B, C, D, R$_3$, R$_4$ and n are as defined hereinbefore, which is treated with a compound of formula (XV):

Hal—(CH$_2$)$_m$—CO—R$_7$  (XV)

wherein m and R$_7$ are as defined for formula (I) and Hal represents halogen,
to yield a compound of formula (I/J):

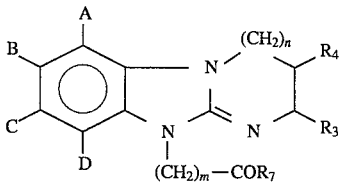
(I/J)

wherein A, B, C, D, m, n, R$_3$, R$_4$ and R$_7$ are as defined hereinbefore, Y and Z each representing a hydrogen atom, X and R$_2$ forming a bond, and R$_1$ representing a group G$_2$, which compound of formula (I/J) may be subjected to the action of an alkali metal mixed hydride to yield a compound of formula (I/K):

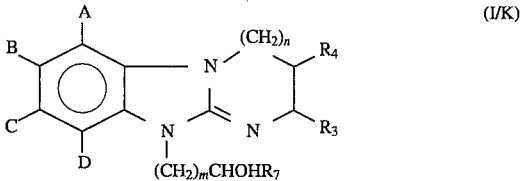
(I/K)

wherein A, B, C, D, m, n, R$_3$, R$_4$ and R$_7$ are as defined hereinbefore, Y and Z each representing a hydrogen atom, X and R$_2$ together forming a bond, and R$_1$ representing a group G$_3$, which compounds of formulae (I/J) or (I/K) are, if necessary, purified and, if desired, converted into salts with a pharmaceutically acceptable acid.

Another means of obtaining compounds of formula (I/J) comprises treating the compound of formula (XIII) as defined hereinbefore with a compound of formula (XV) as defined hereinbefore in order to obtain a compound of formula (XVI):

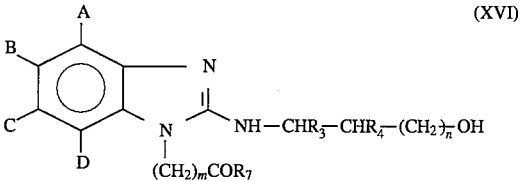
(XVI)

wherein A, B, C, D, R$_3$, R$_4$, n, m and R$_7$ are as defined hereinbefore,
which is treated with a halogenation agent and by heating to yield a compound of formula (I/J) as defined hereinbefore.

Another means of obtaining a compound of formula (I/J) or (I/K) comprises using as starting material a compound of formula (XIV) (and not a compound of formula XIII), which is treated as described hereinbefore.

Another means of obtaining a compound of formula (I/K) comprises treating the compound of formula (XIV) as defined hereinbefore with a compound of formula (XVII):

Hal—(CH$_2$)$_m$—CHOH—R$_7$  (XVII)

wherein Hal, m and R$_7$ are as defined for formula (I).

It is also possible to use as starting material compounds described in the literature of the general formula:

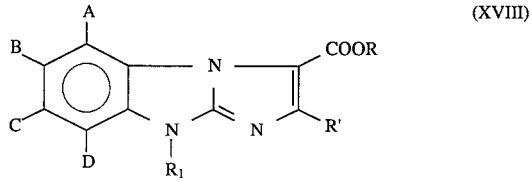
(XVIII)

wherein A, B, C, D and R$_1$ are as defined hereinbefore, R represents a lower alkyl group or hydrogen and R' represents a lower alkyl group optionally substituted by a halogen atom or by a hydroxy group.

Such compounds are described in Khim. Farm., Zh, 1988, 22(7), 815–819 or in Khim. Geterotskl. Soedin., 1973(1), 111–114, or may be obtained by treating a compound of formula (IV), as defined hereinbefore, wherein n is 0 and R$_3$ represents an OR group,
with a compound of formula (XIX):

$$P-\overset{\overset{\displaystyle O}{\|}}{C}-R' \qquad (XIX)$$

wherein P is a leaving group selected from halogen, hydroxy and lower (C$_1$–C$_6$) alkoxy and R' is as defined hereinbefore, to yield, after heating, a compound of formula (XVIII).

When R' represents a methyl group, the compounds (XVIII) are treated with N-bromosuccinimide,
to yield a compound (XVIII') wherein R' represents a CH$_2$Br group.

When R' represents a lower alkyl group substituted by a hydroxy group, treatment with a halogenation agent allows a compound (XVIII'') to be obtained wherein R' represents an alkyl group that is substituted by a halogen atom.

Those compounds (XVIII) (when R' represents a lower alkyl group substituted by a halogen), (XVIII') or (XVIII'') may be treated with an amine of formula HNR$_5$R$_6$ to yield, after heating in acidic medium, a compound of formula (I/L):

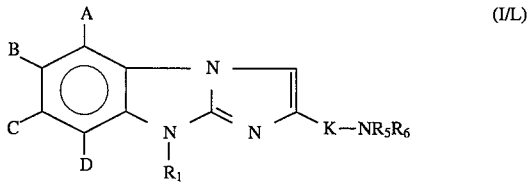
(I/L)

wherein A, B, D, R$_1$, R$_5$ and R$_6$ are as defined for formula (I),
a particular case of compounds of formula (I) wherein Y and Z on the one hand, and X and R$_1$ on the other hand, together form a bond, R$_4$ represents a hydrogen atom, n is 0 and R$_3$ represents a group K—NR$_5$R$_6$ wherein K represents a lower alkylene group, which compound of formula (I/L) is, if desired, converted with an acid into a pharmaceutically acceptable salt.

More generally, the person skilled in the art could use this process, employing compounds of formula (XVIII) as starting material, to obtain other classes of compounds of formula (I) using customary chemical reactions.

Another particular case concerns compounds in which R$_4$ represents a group CH$_2$NR$_5$R$_6$. Those could be obtained by treating a compound of formula (I/A) as defined hereinbefore by means of a Mannich reaction using formaldehyde and an amine $HNR_5R_6$.

Another variant of the general process concerns the synthesis of compounds of formula (I) in which $R_2$ represents a group $G_1$.

Such compounds could be obtained by using as starting material a compound of formula (XX):

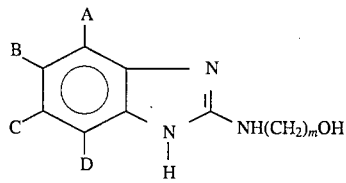

wherein A, B, C, D and m are as defined hereinbefore, which is treated with a compound of formula (XXI):

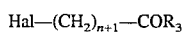

wherein n and $R_3$ are as defined hereinbefore and Hal represents halogen, to yield a compound of formula (XXII):

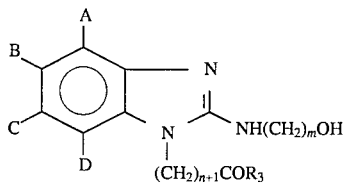

wherein A, B, C, D, $R_3$ and m are as defined for formula (I) which, by means of heating, results in the formation of a compound of formula (XXIII):

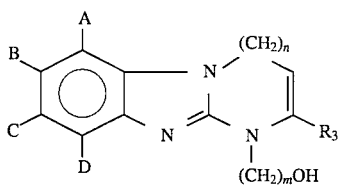

wherein A, B, C, D, m, n and $R_3$ are as defined for formula (I) which is treated:
a) with a halogenation agent,
b) with an amine of formula $HNR_5R_6$,
to enable a compound of formula (I/M) to be obtained:

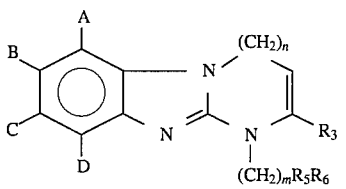

a particular case of compounds of formula (I) wherein A, B, C, D, m, n, $R_3$, $R_5$ and $R_6$ are as defined for formula (I), $R_1$ and X, and Y and Z, in each case representing a bond and $R_2$ representing a group $G_1$, which compound, if necessary, is purified and, if desired, is converted with an acid into a pharmaceutically acceptable salt.

The compounds of formula (I) have valuable pharmacological properties.

Preliminary pharmacological studies have shown that the compounds of the invention are non-toxic and simultaneously have a hypoglycaemic activity and a platelet anti-aggregation activity.

The compounds of the invention thus quite naturally are indicated for diabetes and its cardiovascular complications (retinopathies, peripheral and cerebral vascular disorders).

The present invention also relates to pharmaceutical compositions comprising as active ingredient at least one compound of the general formula I or an addition salt thereof with a pharmaceutically acceptable acid, or, where appropriate, a pharmaceutically acceptable base, alone or combined with one or more inert, non-toxic excipients or carriers.

Of the pharmaceutical compositions according to the invention there may be mentioned more especially those that are suitable for oral, parenteral, nasal, rectal, percutaneous, transcutaneous, ophthalmic, respiratory or perlingual administration etc., and especially tablets, dragees, sublingual tablets, sachets, paquets, gelatin capsules, glossettes, pills, suppositories, creams, ointments, dermic gels, drinkable or injectable ampoules etc..

The dosage varies in accordance with the age and weight of the patient, the nature and severity of the disorder and also the route of administration. The latter may be oral, nasal, rectal or parenteral.

Generally, the unit dose ranges from 0.5 to 20 mg per administration with from one to four administrations in each 24 hours.

The following Examples illustrate the invention and do not limit it in any way.

The $^1H$ nuclear magnetic resonance spectra were carried out using TMS (tetramethylsilane) as internal reference. The chemical shifts are expressed in parts per million (ppm). The infrared spectra were carried out by suspending the product in paraffin oil.

EXAMPLE 1

9-DIETHYLAMINOETHYL-2,3-DIHYDROIMIDAZO[1,2-a]BENZIMIDAZOLE DIHYDROCHLORIDE

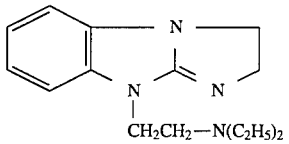

STEP 1: 2-Amino-1-diethylaminoethyl-3-(2-hydroxyethyl) benzimidazole hydrochloride Heat at 130°–135° C. for approximately 40 minutes a mixture of (0.01 mol) of 2-amino-1-[(2-diethylamino)ethyl] benzimidazole obtained as described in J. Med. Chem. 72, 15 (9), 9236, and 3 ml of 2-chloroethanol. After cooling, the reaction mixture is treated with a mixture of ether/acetone until crystallisation occurs. Filter, and wash the residue with ether. Recrystallise from a mixture of alcohol/ether.
Yield: 90%
Melting point: 159° C.
Percentage composition:
Calculated: C 57.6 H 8.1 Cl 11.3 N 17.9
Found: C 57.4 H 8.0 Cl 11.0 N 17.8
STEP 2: 1-Diethylaminoethyl-2-imino-3-(2-chloroethyl)benzimidazole dihydrochloride
Heat at reflux 0.010 mol of the product obtained in Step 1 and 20 mol of thionyl chloride that has previously been dissolved in 15 ml of chloroform. Evaporate the resulting solution, and wash the residue with petroleum ether to yield the title compound. Recrystallisation: ethanol-ether.
Yield: 100%
Melting point: 214°–215° C.

Percentage composition:
Calculated: C 49.0 H 6.9 Cl 28.9 N 15.2
Found: C 49.2 H 6.7 Cl 28.5 N 15.6
STEP 3: 9-Diethylaminoethyl-2,3-dihydroimidazo[1,2-a] benzimidazole dihydrochloride
Add 10% ammonium hydroxide to 5 mmol of the product obtained in the preceding Step and extract with chloroform; evaporate, add 10 ml of o-xylene, and heat at reflux for one hour. After cooling, filter the precipitate, wash it with petroleum ether, treat with a solution of sodium carbonate and extract twice with chloroform (10 ml each time). The extract is eluted with chloroform on alumina gel. The eluate is evaporated, the residue is dissolved in acetone and the solution so obtained is treated with a solution of ethereal hydrogen chloride. Suction-filter the precipitate and wash with acetone and with ether.
Yield: 92% (hydrate crystals—1H$_2$O)
Melting point: 245°–246° C. (hydrate) (from ethanol)
Percentage composition:
Calculated: C 54.4 H 7.3 Cl 21.4 N 16.9
Found: C 54.2 H 7.2 Cl 21.4 N 16.9
Spectral characteristics:
Infrared: 1665 cm$^{-1}$ vC=N
Nuclear magnetic resonance: (base) (CDCl$_3$)
δ: 0.96 ppm, triplet, 6H, 2CH$_3$
δ: 6.82 ppm, unresolved peaks, 4H, aromatic.

EXAMPLE 2

9-MORPHOLINOETHYL-2,3-DIHYDROIMIDAZO[1,2-a]BENZIMIDAZOLE DIHYDROCHLORIDE
The title compound is obtained by proceeding as in Example 1, but using as starting material 2-amino-1-(2-morpholinoethyl)benzimidazole, obtained as described in Khim. Geterot sikl. Soedin; 69, (5) 869–873, instead of 2-amino-1-(2-diethylaminoethyl)benzimidazole.
Melting point: 282°–83° C.
Percentage Composition:
Calculated: C 52.2 H 6.4 Cl 20.5 N 16.2
Found: C 52.0 H 6.3 Cl 20.3 N 16.4

EXAMPLE 3

9-PHENACYL-2,3-DIHYDROIMIDAZO[1,2-a]BENZIMIDAZOLE HYDROCHLORIDE
STEP A: 2-(2-Hydroxyethylamino)-1-phenacylbenzimidazole dihydrobromide
Heat at reflux for three hours 8.95 g (50 mmol) of 2-(2-hydroxyethylamino)benzimidazole and 10 g of phenacyl bromide in 100 ml of 2-propanol. Allow to cool. Suction-filter the resulting precipitate and wash with acetone. The title compound is obtained.
Yield: 89%
Melting point: 216°–217° C. (decomposition)
Percentage composition:
Calculated: C 54.3 H 4.8 Br 21.2 N 11.2
Found: C 54.1 H 5.0 Br 21.0 N 11.2
Spectral characteristics
Infrared: 1702 cm$^{-1}$ vCO 1675 cm$^{-1}$ vC=NH$^+$.
STEP B: 2-(2-Hydroxyethylamino)-1-phenacylbenzimidazole (base)
Add 22% ammonium hydroxide to 75 ml of a hot solution of the dihydrobromide obtained in Step A in 95° alcohol until a pH of approximately 10 is obtained. The title compound precipitates and is filtered, washed with water and dried.
Yield: 95%
Melting point: 167°–168° C. (decomposition)
Percentage composition:
Calculated: C 69.2 H 5.8 N 14.2
Found: C 69.0 H 5.9 N 14.4
Spectral characteristics:
Infrared: 1525, 1580, 1615 cm$^{-1}$ vC=C and C=N 1700 cm$^{-1}$ vC=O
STEP C: 1-Phenacyl-2-(2-chloroethylamino)benzimidazole hydrochloride
Add 0.7 ml (10 mmol) of freshly distilled thionyl chloride, with stirring, to a suspension of 1.5 g (5 mmol) of the base obtained above in 25 ml of anhydrous chloroform. Heat the resulting solution at reflux for 1 hour. After cooling, the 1-phenacyl-2-(2-chloroethylamino)benzimidazole hydrochloride precipitate is isolated by filtration, washed with petroleum ether and recrystallised from a mixture of ethanol/ether.
Yield: 90%
Melting point: 207°–208° C. (decomposition)
Calculated: C 58.3 H 4.9 Cl 20.2 N 12.0
Found: C 58.0 H 5.0 Cl 19.9 N 12.3
STEP D: 2-(2-Chloroethylamino)-1-phenacylbenzimidazole
The hydrochloride obtained in Step C is treated with an aqueous ammonium hydroxide solution, followed by extraction with chloroform of the resulting free base. Recrystallise the residue from benzene.
Yield: 87%
Melting point: 115°–116° C.
Spectral characteristics:
Infrared: 1680 cm$^{-1}$ vCO 3300 cm$^{-1}$ vNH
STEP E: 9-Phenacyl-2,3-dihydroimidazo[1,2-a]benzimidazole
Heat 0.03 mol of 2-(2-chloroethylamino)-1-phenacylbenzimidazole to a temperature of 135°–140° C. obtained by an oil bath. After complete melting, the reaction mixture is crystallised. The reaction mixture is then cooled and treated with 10 ml of a 22% strength aqueous ammonium hydroxide solution and extracted three times with chloroform. The organic phases are combined and concentrated. The organic residue is eluted on a column of alumina and the eluate, after evaporation of the solvent, forms the title compound.
Yield: 88%
Melting point: 178°–179° C.
Percentage composition:
Calculated: C 73.3 H 5.4 N 15.2
Found: C 73.3 H 5.5 N 15.0
Spectral characteristics
Infrared: 1505, 1600 cm$^{-1}$ vC=C 1665 cm$^{-1}$ vC=N 1690 cm$^{-1}$ vC=O
Nuclear magnetic resonance: CDCl$_3$, δ=ppm δ=5.1; singlet, 2H, CH$_2$—CO δ=6.75, 7.54 and 7.9, three multiplets, 9H, aromatic.
STEP F: 9-Phenacyl-2,3-dihydroimidazo[1,2-a]benzimidazole hydrochloride
Dissolve 0.55 g of the base obtained in Step E in 20 ml of acetone, with the application of heat, until a pH of 2–3 is obtained. Filter the resulting precipitate, wash with acetone and with ether and recrystallise from alcohol.
Yield: 96%
Melting point: 257°–258° C. (decomposition)
Percentage composition:
Calculated: C 65.1 H 5.1 Cl 11.3 N 13.4
Found: C 64.9 H 5.2 Cl 11.0 N 13.1

EXAMPLE 4

9-PHENACYL-2,3-DIHYDROIMIDAZO[1,2-a]BENZIMIDAZOLE (second synthesising process)

Add 10 mmol (1.99 g) of phenacyl bromide to a hot solution of 1H-2,3-dihydroimidazo[1,2-a]benzimidazole, described in J. Med. Chem. 1982, 25(11), 1342–6, in 10 ml of 2-propanol. Heat at reflux for two hours. After cooling, the precipitate is collected by filtration and treated with a 22% strength aqueous ammonium hydroxide solution to yield the title compound.
Yield: 95%
Melting point: 178°–179° C.
That product may be treated in accordance with the protocol of Example 3, Step F, to yield the hydrochloride.

EXAMPLE 5

9-(p-CHLOROPHENACYL)-2,3-DIHYDROIMIDAZO[1,2-a]BENZIMIDAZOLE, HYDROCHLORIDE
The title compound is obtained by proceeding as in Example 4 or as in Example 3, but replacing the phenacyl bromide (Example 3, Step A) with 4'-chlorophenacyl bromide.
Melting point: 294°–295° C.
Percentage composition:
Calculated: C 58.7 H 4.3 Cl 20.4 N 12.1
Found: C 58.7 H 4.4 Cl 19.9 N 12.3
Spectral characteristics:
Infrared: 1500–1600 $cm^{-1}$ vCC 1660 $cm^{-1}$ vC=N 1695 $cm^{-1}$ vC=O
Nuclear magnetic resonance: $CDCl_3$, δ=ppm δ=5.02; singlet, 2H, $CH_2$—CO

EXAMPLE 6

9-(p-METHOXYPHENACYL)-2,3-DIHYDROIMIDAZO[1,2-a]BENZIMIDAZOLE HYDROCHLORIDE
The title compound is obtained by proceeding as in Example 4 or as in Example 3, but replacing the phenacyl bromide (Example 3, Step A) with 4'-methoxyphenacyl bromide.
Melting point: 242°–243° C.
Percentage Composition:
Calculated: C 62.9 H 5.3 Cl 10.3 N 12.2
Found: C 62.7 H 5.2 Cl 10.0 N 12.4
Spectral characteristics:
Infrared (base): 1500–1600 $cm^{-1}$ vC=C 1660 $cm^{-1}$ vC=N 1695 $cm^{-1}$ vC=O
Nuclear magnetic resonance: $CDCl_3$, (base)
δ=3.75, 3H, singlet, $OCH_3$
δ=5.03, 2H, singlet, $CH_2O$
δ=6.75 and 7.90, 8H, 2 multiplets, aromatic

EXAMPLE 7

9-(1-NAPHTHOYLMETHYL)-2,3-DIHYDROIMIDAZO[1,2-a]BENZIMIDAZOLE HYDROCHLORIDE
The title compound is obtained by proceeding as in Example 4 or as in Example 3, but replacing the phenacyl bromide (Example 3, Step A) with naphthoylmethyl bromide.
Melting point: 202° C. (decomposition)
Percentage composition:
Calculated: C 64.7 H 5.7 Cl 11.2 N 13.3
Found: C 64.9 H 5.6 Cl 10.9 N 13.4
Spectral characteristics:
Infrared (base): 1665 $cm^{-1}$ vCN 2700–3055 $cm^{-1}$ vCH

EXAMPLE 8

9-(2-HYDROXY-2-PHENYLETHYL)-2,3-DIHYDROIMIDAZO[1,2-a]BENZIMIDAZOLE HYDROCHLORIDE
Add bit by bit 0.3 g (7.5 mmol) of sodium borohydride to a suspension of 1.94 g (7 mmol) of 9-phenacyl-2,3-dihydroimidazo[1,2-a]benzimidazole in 15 ml of methanol over a period of thirty minutes at room temperature. Continue stirring for a further four hours and leave until the next day. Add 10 ml of 10% hydrochloric acid until a pH of 2–3 is obtained and evaporate the methanol. Treat the residue with a solution of ammonium hydroxide and extract with chloroform. Recrystallise from ethanol the residue from extraction.
Yield: 87%
Melting point: 192° C.
Percentage Composition:
Calculated: C 73.0 H 6.7 N 15.0
Found: C 73.2 H 5.8 N 15.3
Spectral characteristics:
Infrared (base): 1665 $cm^{-1}$ vC=N 2700–3055 $cm^{-1}$ vOH
The hydrochloride is obtained by adding ethereal hydrogen chloride to a hot ethanolic solution of the base obtained above (3 mmol, 0.84 g) until an acidic mixture is obtained. Allow to cool, suction-filter and wash with ether.
Yield: (in relation to the base) 97.3%
Melting point: 202° C.
Percentage composition:
Calculated: C 64.7 H 5.7 Cl 11.2 N 13.3
Found: C 64.9 H 5.6 Cl 10.9 N 13.4
Spectral characteristics:
Infrared (base): 1665 $cm^{-1}$ vC=N 2700–3055 $cm^{-1}$ vOH

EXAMPLE 9

9-[2-HYDROXY-2-(4-CHLOROPHENYL)ETHYL]-2,3-DIHYDROIMIDAZO[1,2-a]BENZIMIDAZOLE HYDROCHLORIDE
The title compound is obtained by proceeding as in Example 8, but replacing the 9-phenacyl-2,3-dihydroimidazo[1,2-a]benzimidazole with 9-(p-chlorophenacyl)-2,3-dihydroimidazo[1,2-a]benzimidazole obtained in Example 5.
Melting point (hydrochloride) 208°–209° C.
Percentage composition:
Calculated: C 58.3 H 4.9 Cl 20.2 N 12.0
Found: C 58.4 H 4.7 Cl 20.5 N 11.8
Spectral characteristics:
Infrared (base): 1650 $cm^{-1}$ vC=N 2690–3060 $cm^{-1}$ vOH

EXAMPLE 10

9-[2-(1-NAPHTHYL)-2-HYDROXYETHYL]-2,3-DIHYDROIMIDAZO[1,2-a]BENZIMIDAZOLE HYDROCHLORIDE
The title compound is obtained by proceeding as in Example 8, but replacing the 9-phenacyl-2,3-dihydroimidazo[1,2-a]benzimidazole with 9-(1-naphthoylmethyl)-2,3-dihydroimidazo[1,2-a]benzimidazole obtained in Example 7.
Melting point (hydrochloride) 214°–215° C.
Percentage composition
Calculated: C 68.9 H 5.5 Cl 9.7 N 11.5
Found: C 68.8 H 5.7 Cl 9.5 N 11.4
Spectral characteristics:
Infrared (base): 1650 $cm^{-1}$ vC=N 2700–3055 $cm^{-1}$ vOH

EXAMPLE 11

9-DIETHYLAMINOETHYL-2-(4-TOLYL)-IMIDAZO[1,2-a]BENZIMIDAZOLE DIHYDROBROMIDE
STEP A: 2-Amino-1-diethylaminoethyl-3-(4-toluoylmethyl)benzimidazolium hydrobromide
Add 2.13 g (10 mmol) of 4-methylphenacyl bromide to a hot solution of 2.32 g of 2-amino-1-diethylaminoethyl benzimidazole in 50 ml of acetone. Stir the mixture carefully for one night at room temperature. The next day, suction-filter the precipitate and wash with acetone.
Yield: 96%
Melting point: 195°–196° C.
Percentage composition:
Calculated: C 59.3 H 6.6 Br 17.9 N 12.6
Found: C 59.3 H 6.5 Br 17.7 N 12.8
Spectral characteristics
Infrared (base): 1690 cm$^{-1}$ νC=0 1670 c,$^{-1}$ νCN 3150, 3310 cm$^{-1}$ νNH$_2$
STEP B: 9-Diethylaminoethyl-2-(4-tolyl)-imidazo[1,2-a]benzimidazole dihydrobromide
The hydrobromide obtained in Step A is heated at the boil in concentrated hydrobromic acid for 2 hours. Cool the reaction mixture and place it in the refrigerator for one night. Suction-filter the title compound, wash with acetone and recrystallise from ethanol.
Melting point: 239° C.
Percentage composition:
Calculated: C 52.0 H 5.6 Br 31.4 N 11.0
Found: C 52.2 H 5.5 Br 31.2 N 11.1
Spectral characteristics:
Infrared (base): 1615, 1605, 1508 cm$^{-1}$ νC=C, νC=N
Nuclear magnetic resonance: $^1$H, (CDCl$_3$)
δ=0.76 ppm, 6H, triplet, 2(CH$_2$CH$_3$)
δ=2.18 ppm, 3H, singlet, C$_6$H$_4$—CH$_3$
δ=2.45 ppm, 4H, quadruplet, 2(CH$_2$—CH$_3$)
δ=7.15–7.48 ppm, unresolved peaks, 9H, aromatic
N.B.: a second portion of hydrobromide (0.35 g) can be obtained by rendering alkaline the mother liquors followed by column chromatography of the base and conversion of the latter into a salt.

EXAMPLE 12

2-TERT-BUTYL-9-(2-MORPHOLINOETHYL)-IMIDAZO[1,2-a]BENZIMIDAZOLE DIHYDROBROMIDE
STEP A: 2-Amino-1-(2-morpholinoethyl)-3-pivaloylmethylbenzimidazolium hydrobromide
A hot solution of 2-amino-1-morpholinoethyl benzimidazole in 25 ml of ethanol is mixed with 1.35 g (10 mmol) of bromopinacolone, heated at reflux for 10 minutes, left at room temperature for 3 hours and diluted twice with acetone. The resulting precipitate is filtered and washed with acetone to yield the title compound.
Yield: 87%
Melting point: 195°–196° C. (decomposition)
Percentage composition:
Calculated: C 53.6 H 6.9 Br 18.8 N 13.2
Found: C 53.5 H 6.7 Br 19.0 N 13.4
Spectral characteristics:
Infrared (base): 1665 cm$^{-1}$ νC=N 1715 cm$^{-1}$ νCO
STEP B: 2-Tert-butyl-9-morpholinoethylimidazo[1,2-a]benzimidazole hydrochloride
The hydrobromide obtained in Step A is heated at reflux in concentrated hydrochloric acid for 30 minutes. The solution is cooled and neutralised with an aqueous ammonium hydroxide solution. The reaction mixture is extracted with benzene and the extract is dried over sodium sulfate. Subsequently, pass through a stream of gaseous hydrochloric acid until acidity. The resulting precipitate is filtered and recrystallised from ethanol.
Yield: 87%
Melting point: 263°–264° C.
Percentage composition:
Calculated: C 57.1 H 7.1 Br 17.8 N 14.0
Found: C 57.0 H 6.9 Br 17.5 N 14.2
Spectral characteristics:
Infrared (base): 1505, 1600, 1620 cm$^{-1}$ νC=C νC=N

EXAMPLE 13

2-TERT-BUTYL-9-(2-MORPHOLINOETHYL)-IMIDAZO[1,2-a]BENZIMIDAZOLE HYDROBROMIDE
The title compound is obtained by proceeding as in Example 12, but replacing the stream of gaseous hydrochloric acid in Step B with a stream of gaseous hydrobromic acid.
Melting point: 294°–295° C.
Percentage composition:
Calculated: C 46.7 H 5.8 Br 32.4 N 11.5
Found: C 46.5 H 6.0 Br 32.4 N 11.6

EXAMPLE 14

2-TERT-BUTYL-9-(3-DIMETHYLAMINOPROPYL)-IMIDAZO[1,2-a]BENZIMIDAZOLE DIHYDROCHLORIDE
STEP A: 2-Amino-1-(3-dimethylaminopropyl)-3-pivaloylmethylbenzimidazolium
React 10 mmol (2.18 g) of 2-amino-1-dimethylaminopropylbenzimidazole and 10 mmol (1.35 ml) of bromopinacoline in 70 ml of acetone.
Recrystallisation: ethanol/acetone/ether
Yield: 90%
Melting point: 197°–198° C. (decomposition)
Percentage composition:
Calculated C 54.4 H 7.4 Br 20.1 N 14.1
Found: C 54.2 H 7.4 Br 19.8 N 14.1
Spectral characteristics
Infrared: 1720 cm$^{-1}$ νC=0 1660 cm$^{-1}$ νC=N 3050, 3250 cm$^{-1}$ νNH
STEP B: 2-Tert-butyl-9-(3-dimethylaminopropyl)imidazo[1,2-a]benzimidazole
Heat at reflux for 25 minutes 3 mmol of the hydrobromide obtained in Step A and 4 g of sodium carbonate in 25 ml of ethanol. Evaporate, treat the residue twice with 10 ml of chloroform each time, and pass the resulting chloroform solutions over a column of alumina. Evaporate the eluate. The title compound is obtained in the form of an oil.
Yield: 90%
Percentage composition:
Calculated: C 72.4 H 8.8 N 18.8
Found: C 72.2 H 8.7 N 18.9
Spectral characteristics:
Infrared: 1510, 1605, 1625 cm$^{-1}$ νC=C νC=N
STEP C: 2-Tert-butyl-9-(3-dimethylaminopropyl) imidazo[1,2-a]benzimidazole dihydrochloride
Dissolve the oil obtained in Step B in 15 ml of anhydrous ether and acidify with ethereal hydrogen chloride. Filter the resulting precipitate and purify by means of reprecipitation with ether from an ethanolic solution.
Yield: 92%
Melting point: 258°–259° C.
Percentage composition:
Calculated: C 58.2 H 7.6 Cl 19.1 N 15.1
Found: C 57.9 H 7.8 Cl 18.8 N 15.2

EXAMPLE 15

2-TERT-BUTYL-9-(3-DIMETHYLAMINOPROPYL)-IMIDAZO[1,2-a]BENZIMIDAZOLE DIPERCHLORATE
The title compound is obtained by proceeding as in Example 14 but replacing the hydrochloric acid in Step C with perchloric acid.
Melting point: 236°–237° C.

Percentage composition:
Calculated: C 43.3 H 5.7 Cl 14.2 N 11.2
Found: C 43.2 H 5.5 Cl 14.0 N 11.0

EXAMPLE 16

9-(2-MORPHOLINOETHYL)-2-(4-HYDROXYPHENYL)-IMIDAZO[1,2-a]BENZIMIDAZOLE DIHYDROCHLORIDE

Step A: 9-(2-Morpholinoethyl)-2-(4-hydroxyphenyl)-imidazo [1,2-a]benzimidazole
A mixture of 2-amino-1-(2-morpholinoethyl) benzimidazole (10 mmol, 2.46 g) and 4-hydroxyphenacyl bromide (10 mmol, 2.15 g) (obtained by bromination of para-hydroxyacetophenone with cupric bromide in a mixture of chloroform and ethyl acetate) is heated at reflux for 1 hour in 10 ml of dimethylformamide. After cooling, the mixture is poured into 50 ml of water and rendered alkaline with ammonium hydroxide. The resulting oil is removed and treated with water. The crystallised residue is filtered, dried, and recrystallised from ethanol.
Yield: 52%
Melting point: 228°–229° C.
Percentage composition:
Calculated: C 69.6 H 6.1 N 15.5
Found: C 69.5 H 6.2 N 15.5
Spectral characteristics:
Infrared: 3350–3200 cm$^{-1}$ vOH 1500, 1600, 1605 cm$^{-1}$ vC=C vC=N
Nuclear magnetic resonance: $^1$H, (CDCl$_3$)
δ=2.48 ppm, triplet, 4H, N(CH$_2$)$_2$ morpholine
δ=2.78 ppm, triplet, 2H, CH$_2$—(morpholine)
δ=3.56 ppm, triplet, 4H, (CH$_2$)$_2$O
δ=4.26 ppm, triplet, 2H, N-CH$_2$—CH$_2$-morpholine
δ=6.85–7.45 ppm, multiplet, 9H, aromatic
Step B: 9-(2-Morpholinoethyl)-2-(4-hydroxyphenyl)-imidazo [1,2-a]benzimidazole dihydrochloride
Heat 5 mmol (1.81 g) of the base obtained in Step A in 10 ml of ethanol and acidify with a hydrochloric acid isopropanol solution. Cool, filter, wash with ethanol and with acetone and recrystallise from a mixture of ethanol and water.
Yield: 81%
Melting point: 276°–277° C.
Percentage composition:
Calculated: C 57.9 H 5.6 Cl 16.3 N 12.9
Found: C 57.7 H 5.5 Cl 16.0 N 12.8
That compound can also be obtained by using the procedure in Example 11 but, in Step A, replacing:
  4-methylphenacyl bromide with 4-methoxyphenacyl bromide, and
  2-amino-1-[(2-diethylamino)ethyl]benzimidazole with 2-amino-1-[(2-morpholino)ethyl]benzimidazole.
The cyclisation reaction in the boiling hydrobromic acid is accompanied by hydrolysis of the methoxy group, and in that manner the hydrobromide is obtained.

EXAMPLE 17

9-(2-MORPHOLINOETHYL)-2-(3-HYDROXYPHENYL)-IMIDAZO[1,2-a]BENZIMIDAZOLE DIHYDROBROMIDE
The title compound is obtained by proceeding as in Example 11 but, in Step A, replacing:
  4-methylphenacyl bromide with 3-methoxyphenacyl bromide and
  2-amino-1-(2-diethylaminoethyl)benzimidazole with 2-amino-1-(2-morpholinoethyl)benzimidazole.
Melting point: 275°–277° C.
Percentage composition:
Calculated: C 48.1 H 4.6 Br 30.5 N 10.7
Found: C 48.2 H 4.5 Br 30.2 N 10.5

EXAMPLES 18 TO 24

By proceeding as in Example 11, but using as starting materials:
  appropriately substituted benzimidazole compounds,
  appropriately substituted aroylmethyl halides, the following are obtained:

EXAMPLE 18

9-DIETHYLAMINOETHYL-2-(3,4-DIMETHOXYPHENYL)-IMIDAZO[1,2-a]BENZIMIDAZOLE SULFATE
Melting point: 248°–249° C. (decomposition)
Percentage composition:
Calculated: C 56.3 H 6.2 N 11.4 S 6.5
Found: C 56.2 H 6.0 N 11.5 S 6.3
Spectral characteristics
Infrared: 1510, 1600, 1610 cm$^{-1}$ (vC=C vC=N)
Nuclear magnetic resonance: (CDCl$_3$)
δ=0.92 ppm, triplet, 6H, 2(OCH$_3$)
δ=2.54 ppm, quadruplet, 4H, 2(CH$_2$—CH$_3$)
δ=2.88 ppm, triplet, 2H, CH$_2$CH$_2$N(Et)$_2$
δ=4.20 ppm, triplet, 2H, CH$_2$CH$_2$N(Et)$_2$

EXAMPLE 19

9-DIETHYLAMINOETHYL-2-(3,4-DIHYDROXYPHENYL)-IMIDAZO[1,2-a]BENZIMIDAZOLE DINITRATE
Melting point: 198°–199° C. (decomposition)
Percentage composition:
Calculated: C 51.4 H 5.3 N 17.1
Found: C 51.2 H 5.4 N 17.2
Spectral characteristics:
Infrared: 1510, 1590, 1605 cm$^{-1}$ vC=C vC=N 3200–3350 cm$^{-1}$ vOH

EXAMPLE 20

9-(2-DIETHYLAMINOETHYL)-2-(3,4-DIHYDROXYPHENYL)-IMIDAZO[1,2-a]BENZIMIDAZOLE HYDROCHLORIDE
Melting point: 276°–278° C.
Percentage composition:
Calculated: C 57.7 H 6.0 Cl 16.2 N 12.8
Found: C 57.5 H 6.3 Cl 16.6 N 13.0
Spectral characteristics:
Infrared: 1510, 1590, 1605 cm$^{-1}$ vC=C vC=N 3200–3350 cm$^{-1}$ vOH

EXAMPLE 21

9-(2-PIPERIDINOETHYL)-2-(3,4-DIHYDROXYPHENYL)-IMIDAZO[1,2-a]BENZIMIDAZOLE DIHYDROBROMIDE
Melting point: 297°–298° C. (decomposition)
Percentage composition:
Calculated: C 49.1 H 4.9 Br 29.7 N 10.4
Found: C 48.9 H 5.2 Br 29.5 N 10.3

EXAMPLE 22

9-(2-PIPERIDINOETHYL)-2-(3,4-DIHYDROXYPHENYL)-IMIDAZO[1,2-a]BENZIMIDAZOLE DINITRATE
Melting point: 215°–216° C.
Percentage composition:

Calculated: C 52.6 H 5.2 N 16.7
Found: C 52.4 H 5.2 N 16.7
Spectral characteristics:
Infrared (base): 1500, 1595, 1605 cm$^{-1}$ vC=C vC=N
3200–3600 cm$^{-1}$ vOH

EXAMPLE 23

9-(2-PIPERIDINOETHYL)-2-(3,4-DIHYDROXYPHENYL)-IMIDAZO[1,2-a]BENZIMIDAZOLE DIHYDROCHLORIDE
Melting point: 293°–294° C.
Percentage composition:
Calculated: C 58.8 H 5.8 Cl 15.8 N 12.5
Found: C 58.6 H 5.8 Cl 15.7 N 12.7

EXAMPLE 24

9-(2-DIETHYLAMINOETHYL)-2-(1-METHYL-2-BENZIMIDAZOLYL)IMIDAZO[1,2-a]BENZIMIDAZOLE DIHYDROBROMIDE HYDRATE
Melting point: 280°–281° C.
Percentage composition:
Calculated: C 48.8 H 5.3 Br 28.2 N 14.9
Found: C 48.6 H 5.5 Br 28.4 N 14.7

EXAMPLE 25

9-(2-DIETHYLAMINOETHYL)-2-(2-THIENYL)-IMIDAZO[1,2-a]BENZIMIDAZOLE DIPERCHLORATE
Melting point: 139°–140° C.
Spectral characteristics: $^1$H NMR (CF$_3$COOD)
δ=1.00 ppm, 6H, triplet, 2CH$_3$
δ=3.14 ppm, 4H, quadruplet, 2 CH$_2$—CH$_3$
δ=3.49 ppm, 2H, triplet, CH$_2$N—(CH$_2$CH$_3$)$_2$
δ=4.60 ppm, 2H, triplet, CH$_2$CH$_2$N(CH$_2$CH$_3$)$_2$

EXAMPLE 26

9-(2-DIETHYLAMINOETHYL)-2-(2-THIENYL)-IMIDAZO[1,2-a]BENZIMIDAZOLE PHOSPHATE
Melting point: 188°–189° C. (decomposition)
Spectral characteristics: $^1$H NMR (CF$_3$COOD)
δ=1.10 ppm, 6H, triplet, 2CH$_3$
δ=3.18 ppm, 4H, quadruplet, 2 CH$_2$—CH$_3$
δ=3.53 ppm, 2H, triplet, CH$_2$N—(CH$_2$CH$_3$)$_2$
δ=4.70 ppm, 2H, triplet, CH$_2$CH$_2$N(CH$_2$CH$_3$)$_2$

EXAMPLE 27

9-(2-PIPERIDINOETHYL)-2-(2-THIENYL)-IMIDAZO[1,2-a]BENZIMIDAZOLE DIHYDROBROMIDE
Melting point: 295.5°–296° C. (decomposition)
Percentage composition:
Calculated: C 46.9 H 4.7 Br 31.2 N 10.9 S 6.3
Found: C 47.0 H 4.9 Br 30.9 N 10.9 S 6.3
Spectral characteristics
Infrared (base): 1500, 1600, 1615 cm$^{-1}$ vC=C vC=N
3200–3600 cm$^{-1}$ vOH

EXAMPLE 28

9-(2-PIPERIDINOETHYL)-2-(2-THIENYL)-IMIDAZO[1,2-a]BENZIMIDAZOLE SULFATE
Melting point: 265°–266° C. (decomposition)
Percentage composition:
Calculated: C 53.5 H 5.4 N 12.5 S 14.3
Found: C 53.4 H 5.7 N 12.7 S 14.5

EXAMPLE 29

9-(2-PIPERIDINOETHYL)-2-(5-BROMO-2-THIENYL)-IMIDAZO[1,2-a]BENZIMIDAZOLE DIHYDROCHLORIDE
STEP A: 2-Amino-3-(5-bromo-2-thenoylmethyl)-1-(2-piperidinoethyl)-benzimidazole hydrobromide
Add a solution of 5-bromo-2-bromoacetylthiophene (5.68 g, 20 mmol) in 30 ml of ether to a hot solution of 2-amino-1-(2-piperidinoethyl)-benzimidazole (4.88 g, 20 mmol) in 150 ml of acetone. Stir and maintain at room temperature for five hours. Suction-filter the precipitate, wash with acetone and then with ether to obtain the title compound.
Yield: 82%
Melting point: 185° C. (decomposition)
Percentage composition
Calculated: C 45.4 H 4.6 Br 30.2 N 10.6 S 6.1
Found: C 45.3 H 4.8 Br 30.6 N 10.7 S 6.5
Spectral characteristics:
Infrared (base): 1680 cm$^{-1}$ vC=N 1695 cm$^{-1}$ vCO 3120, 3315 cm$^{-1}$ vNH$_2$
STEP B: 9-(2-Piperidinoethyl)-2-(5-bromo-2-thienyl)imidazo[1,2-a]benzimidazole dihydrochloride
The hydrobromide obtained in Step A is heated at melting for 20 minutes at 190° C. After cooling, the resulting product is treated with 10 ml of ammonium hydroxide and extracted with benzene. The organic phases are combined, concentrated and passed over a column of alumina eluted with benzene. Acidify the eluant with a solution of ethereal hydrogen chloride. The resulting precipitate is suction-filtered, washed with acetone and then with ether and recrystallised from ethanol.
Yield: 72%
Melting point: 240°–241° C. (decomposition)
Percentage composition:
Calculated: C 47.8 H 4.6 Br 15.9 Cl 14.1 N 11.2 S 6.4
Found: C 47.6 H 4.7 Br 15.8 Cl 14.3 N 11.0 S 6.2
Spectral characteristics:
Infrared: 1503, 1595, 1615 cm$^{-1}$ vC=C vC=N

EXAMPLE 30

2-(5-BROMO-2-THIENYL)-9-(2-MORPHOLINOETHYL)-IMIDAZO[1,2-a]BENZIMIDAZOLE DIHYDROCHLORIDE
STEP A: 2-Amino-3-(5-bromo-2-thenoylmethyl)-1-(2-morpholinoethyl)benzimidazole hydrobromide
Dissolve 2.46 g (10 mmol) of 2-amino-1-(2-morpholinoethyl)benzimidazole in 120 ml of acetone with heating. Subsequently, add 5-bromo-2-bromoacetylthiophene. After stirring, leave at room temperature for 3 to 4 hours. The 2-amino-3-(5-bromo-2-thenoylmethyl)-1-(2-morpholinoethyl)benzimidazole hydrobromide precipitate is filtered, washed twice with 20 ml of acetone each time and with ether (20 ml) to obtain 4.7 g of the title compound.
Yield: 88%
Melting point: 207°–208° C.
Percentage composition:
Calculated: C 43.0 H 4.2 Br 30.1 N 10.6 S 6.1
Found: C 43.3 H 4.3 Br 30.5 N 10.5 S 5.9
Spectral characteristics:
Infrared: 1690 cm$^{-1}$ vC=O 1680 cm$^{-1}$ vC=N 3120, 3310 cm$^{-1}$ vNH$_2$
STEP B: 2-(5-Bromo-2-thienyl)-9-(2-morpholinoethyl)imidazo[1,2-a]benzimidazole
The hydrobromide obtained in Step A is heated at reflux for 9 hours in 50 ml of water in the presence of 2.1 g of sodium hydrogen carbonate. The resulting oil is extracted three times with 15 ml of chloroform each time; the organic phases are combined and concentrated by evaporation and then the residue is purified by chromatography on a column of alumina eluted with chloroform. The first fraction constitutes the title compound.
Melting point: 187° C.
Percentage composition:
Calculated: C 52.9 H 4.4 Br 18.5 N 13.0 S 7.4
Found: C 53.0 H 4.5 Br 18.2 N 13.3 S 7.2
Spectral characteristics:
Infrared: 1500, 1595, 1620 cm$^{-1}$ vC=C vC=N
Spectral characteristics: NMR (CDCl$_3$)
δ=2.46 ppm, triplet, 4H, N(CH$_2$)$_2$ (morpholine)
δ=2.76 ppm, triplet, 2H, CH$_2$-morpholine
δ=3.56 ppm, triplet, 4H, (CH$_2$)$_2$O (morpholine)
δ=4.22 ppm, triplet, 2H, CH$_2$CH$_2$-morpholine
STEP C: 2-(5-Bromo-2-thienyl)-9-(2-morpholinoethyl)imidazo[1,2-a]benzimidazole dihydrochloride
The base obtained in the preceding Step is dissolved in acetone (6 mmol per 50 ml) which is acidified with concentrated hydrochloric acid. Thirty minutes later, the resulting precipitate is filtered, and washed with acetone and with ether.
Yield: 91%
Melting point: 237°–238° C. (decomposition)
Percentage composition:
Calculated: C 45.3 H 4.2 Br 15.8 Cl 14.1 N 11.1 S 6.4
Found: C 45.0 H 4.3 Br 15.4 Cl 14.4 N 11.4 S 6.2

EXAMPLE 31

2-(2-FURYL)-9-(2-N,N-DIETHYLAMINOETHYL)-IMIDAZO[1,2-a]BENZIMIDAZOLE DIHYDROBROMIDE
The title compound is obtained by proceeding as in Example 30, but replacing:
1- in Step A
  2-amino-1-(2-morpholinoethyl)benzimidazole with 2-amino-1-(2-N,N-diethylaminoethyl)benzimidazole
  and 5-bromo-2-bromoacetylthiophene with 2-bromoacetylfuran,
2- in Step C
  hydrochloric acid with hydrobromic acid.
Melting point: 269°–270° C. (decomposition)
Spectral characteristics: $^1$H NMR (CF$_3$COOH)
δ=1.04 ppm, triplet, 6H, (2CH$_3$)
δ=3.10 ppm, quadruplet, 4H, (2CH$_2$)
δ=3.48 ppm, triplet, 2H, CH$_2$N(Et)$_2$
δ=4.90 ppm, triplet, 2H, CH$_2$CH$_2$N(Et)$_2$

EXAMPLE 32

2-(2-FURYL)-9-(2-N,N-DIETHYLAMINOETHYL)-IMIDAZO[1,2-a]BENZIMIDAZOLE SULFATE
The title compound is obtained by proceeding as in Example 31 but replacing hydrobromic acid in Step C with sulfuric acid.
Melting point: 239°–240° C. (decomposition)
Percentage composition:
Calculated: C 54.3 H 5.7 N 13.3 S 7.6
Found: C 54.3 H 6.0 N 13.5 S 8.0
Spectral characteristics
Infrared: 1500, 1595, 1620 cm$^{-1}$ vC=C vC=N

EXAMPLE 33

2-(2-FURYL)-9-(2-MORPHOLINOETHYL)-IMIDAZO[1,2-a]BENZIMIDAZOLE DIHYDROBROMIDE
The title compound is obtained by proceeding as in Example 30 but replacing the 5-bromo-2-bromoacetylthiophene in Step A with 2-bromoacetylfuran and the hydrochloric acid in Step C with hydrobromic acid.
Melting point: 263°–264° C. (decomposition)
Percentage composition:
Calculated: C 45.6 H 4.5 Br 32.1 N 11.3
Found: C 45.8 H 4.6 Br 31.9 N 11.5
Spectral characteristics
Infrared: 1500, 1600, 1630 cm$^{-1}$ vC=C vC=N
Spectral characteristics: $^1$H NMR (CDCl$_3$)
δ=2.48 ppm, triplet, 4H, N(CH$_2$)$_2$ morpholine
δ=2.79 ppm, triplet, 2H, CH$_2$-morpholine
δ=3.57 ppm, triplet, 4H, (CH$_2$)$_2$O (morpholine)
δ=4.26 ppm, triplet, 2H, CH$_2$CH$_2$ morpholine

EXAMPLE 34

9-BENZYL-2-DIETHYLAMINOMETHYLIMIDAZO[1,2-a]BENZIMIDAZOLE DIHYDROCHLORIDE
STEP A: 9-Benzyl-2-diethylaminomethyl-3-ethoxycarbonylimidazo[1,2-a]benzimidazole
Add 1.04 ml (10 mmol) of diethylamine to a hot solution of 9-benzyl-2-bromomethyl-3-ethoxycarbonylimidazo[1,2-a]benzimidazole (2.01 g, 5 mmol), prepared as described for the alkylated analogues in Khim. Farm. ZH 88, 22 (7), 815–9, in 20 ml of benzene. Heat at reflux for one hour, cool. Remove the resulting precipitate, evaporate the benzene, and the residue is recrystallised by hexane to yield the title compound.
Yield: 96%
Melting point: 44°–45° C.
Percentage composition:
Calculated: C 71.3 H 7.0 N 13.9
Found: C 71.3 H 7.2 N 14.1
Spectral characteristics
Infrared: 1700 cm$^{-1}$ vC=O 1490, 1590, 1605 cm$^{-1}$ vC=C vC=N
STEP B: 9-Benzyl-2-diethylaminomethylimidazo[1,2-a]benzimidazole dihydrochloride
The compound obtained in the preceding Step is dissolved in 35 ml of concentrated hydrobromic acid and heated at reflux for 10 hours. After cooling, render alkaline using ammonium hydroxide until a pH of 8–9 is reached. Extract with chloroform and pass the residue over a column of alumina. Elute with chloroform. The oil obtained after evaporation of the solvent is dissolved in 20 ml of acetone and the resulting solution is acidified with ethereal hydrogen chloride. Leave for 2 hours and filter the resulting precipitate; wash with acetone and purify by reprecipitating with ether an ethanolic solution.
Yield: 61%
Melting point: 215°–216° C. (decomposition)
Percentage composition:
Calculated: C 57.1 H 6.9 Cl 16.1 N 12.7
Found: C 57.3 H 7.2 Cl 15.7 N 12.5
Spectral characteristics:
Infrared: 1620, 1600, 1490 cm$^{-1}$ vC=C vC=N

EXAMPLE 35

2,9-DIMETHYL-3-(-DIMETHYLAMINOPROPOXY-CARBONYL)-IMIDAZO[1,2-a]BENZIMIDAZOLE DIHYDROBROMIDE

STEP A: 2,9-Dimethyl-3-trichloroacetylimidazo[1,2-a]benzimidazole

Pour 5.45 g (30 mmol) of freshly distilled trichloroacetyl chloride dropwise into a boiling solution of 2,9-dimethylimidazo[1,2-a]benzimidazole (3.7 g; 20 mmol)—obtained as described in Khim. Geterotsikl Soedin, 86, (7), 918–925—in 50 ml of xylene, with vigorous stirring, over a period of 20 to 30 minutes. The mixture is then heated at reflux for two hours until the product which has initially precipitated is completely dissolved. Cool and filter. Concentrate the mother liquors and add petroleum ether. Combine with the precipitate obtained earlier and repeat the operation. The combined precipitates are treated with an aqueous solution of sodium hydrogen carbonate and then recrystallised from ethyl acetate.

Yield: 76%
Melting point: 187°–188° C. (decomposition)
Percentage composition:
Calculated: C 47.2 H 3.0 Cl 32.2 N 12.7
Found: C 47.6 H 3.1 Cl 32.0 N 12.9
Spectral characteristics
Infrared: 1635 cm$^{-1}$ vC=O STEP B: 2,9-Dimethyl-3-(v-dimethylaminopropoxycarbonyl)imidazo[1,2-a]benzimidazole dihydrobromide The sodium alkoxide (obtained from 0.5 g of sodium and 2.5 ml (20 mmol) of v-dimethylaminopropanol in 40 ml of benzene) is added dropwise to a suspension of 2.31 g (7 mmol) of the trichloroketone obtained in the preceding Step in 30 ml of benzene. Heat that mixture until the ketone crystals disappear. Evaporate, treat the residue with 20 ml of water and extract three times with 10 ml of chloroform each time. Concentrate the organic phases and purify by passing over a column of alumina (eluant: chloroform) to obtain 2 g (yield 91%) of 3-(v-dimethylaminopropoxycarbonyl)-2,9-dimethylimidazo [1,2-a]benzimidazole. The oil so obtained is dissolved in 25 ml of acetone and the solution is acidify with concentrated hydrobromic acid. Collect the precipitate and wash with acetone and with ether.

Melting point: 198° C.
Percentage composition:
Calculated: C 42.9 H 5.1 Br 33.6 N 11.8
Found: C 42.7 H 5.0 Br 32.3 N 11.8
Spectral characteristics
Infrared: 1700 cm$^{-1}$ vC=O.

EXAMPLE 36

3-DIETHYLAMINOMETHYL-2,6,7-TRIMETHYL-9-ETHYLIMIDAZO[1,2-a]BENZIMIDAZOLE DIHYDROCHLORIDE

STEP A: 3-Diethylaminomethyl-2,6,7-trimethyl-9-ethylimidazo[1,2-a]benzimidazole

A solution of 1.5 g (6.5 mmol) of 2,6,7-trimethyl-9-ethylimidazo[1,2-a]benzimidazole in 8 ml of ethanol is mixed with 0.6 ml (7.5 mmol) of 40% formaldehyde and diethylamine (0.76 ml, 7.5 mmol). Stir at room temperature. Once the reaction is complete (verified by thin- layer chromatography), evaporate, wash the residue with water, dry, and recrystallise from petroleum ether.

Yield: 93%
Melting point: 117° C.
Percentage composition:
Calculated: C 73.0 H 9.0 N 18.0
Found: C 73.2 H 9.0 N 17.9
Spectral characteristics:
Infrared: 1500, 1595, 1605 cm$^{-1}$ vC=C vC=N STEP B: 3-Diethylaminomethyl-2,6,7-trimethyl-9-ethylimidazo-[1,2-a]benzimidazole dihydrochloride Dissolve 1.86 g (6 mmol) of the base obtained in Step A in 20 ml of acetone and add concentrated hydrochloric acid. An oil appears which, by means of trituration, allows a precipitate to be obtained which is purified by reprecipitation with ether from an ethanolic solution.

Yield: 92%
Melting point: 130°–135° C. (decomposition)
Percentage composition:
Calculated: C 59.2 H 7.9 Cl 18.4 N 14.5
Found: C 59.1 H 8.0 Cl 18.2 N 14.6

EXAMPLE 37

3-DIMETHYLAMINOMETHYL-2-PHENYL-9-ETHYLIMIDAZO[1,2-a]BENZIMIDAZOLE DIHYDROCHLORIDE

The title compound is obtained by proceeding as in Example 36 but replacing, on the one hand, 2,6,7-trimethyl-9-ethylimidazo[1,2-a]benzimidazole by the 9-methyl homologue (obtained by a process identical to that described in Khim Geterstskil. Soedin 86, 7, 918–925) and, on the other hand, diethylamine by dimethylamine.

Melting point: 159°–160° C. (decomposition)
Percentage composition:
Calculated: C 61.4 H 6.2 Cl 18.1 N 14.3
Found: C 61.2 H 6.2 Cl 18.0 N 14.2

EXAMPLE 38

3-PIPERIDINOMETHYL-2-PHENYL-9-ETHYLIMIDAZO[1,2-a]BENZIMIDAZOLE DIHYDROCHLORIDE

The title compound is obtained by proceeding as in Example 37 but replacing the dimethylamine with piperidine.

Melting point: 154°–155° C. (decomposition)
Percentage composition:
Calculated: C 64.0 H 6.6 Cl 16.4 N 13.0
Found: C 64.2 H 6.6 Cl 16.1 N 13.3

EXAMPLE 39

2-METHYL-9-(2-MORPHOLINOETHYL)-3-(4-CHLOROBENZOYL)-IMIDAZO [1,2-a]BENZIMIDAZOLE DIHYDROCHLORIDE

STEP A: 2-Amino-4-(4-chlorophenacyl)-1-(2-morpholinoethyl)benzimidazolium bromide A solution of 2.33 g (10 mmol) of 4-chlorophenacyl bromide in 25 ml of acetone is added to a hot solution of 2-amino-1-(2-morpholinoethyl)benzimidazole (2.46 g, 10 mmol) in 75 ml of acetone. The mixture is stirred, heated at the boil for 5 minutes and maintained at room temperature. Three hours later a precipitate of the title compound appears, which is filtered and washed with acetone and with ether.

Yield: 95%
Melting point: 193°–194° C.
Percentage composition:
Calculated: C 52.6 H 5.0 Br 16.6 Cl 7.4 N 11.7
Found: C 52.5 H 5.1 Br 16.2 Cl 7.7 N 11.9
Spectral characteristics:
Infrared: 1700 cm$^{-1}$ vC=O 1680 cm$^{-1}$ vC=C 3170 cm$^{-1}$ vNH$_2$ STEP B: 2-Methyl-9-(2-morpholinoethyl)-3-(4-chlorobenzoyl) imidazo[1,2-a]benzimidazole 2.4 g of the product obtained in Step A are suspended in 25 ml of acetic anhydride and maintained at room temperature for 24 hours. The reaction mixture is then heated in a bain-marie until the precipitate that has formed is dissolved, and is then heated at reflux for 10 minutes. After cooling, the solution is poured into 100 ml of water and, after decomposition of the excess acetic anhydride with ammonium hydroxide, extracted twice with benzene. The combined extracts are concentrated and passed over a column of alumina (eluant: benzene). The eluant is evaporated to yield the title compound.
Yield: 86%
Melting point: 147°–148° C.
Percentage composition:
Calculated: C 65.3 H 5.5 Cl 8.4 N 13.3
Found: C 65.4 H 5.7 Cl 8.2 N 13.0
Spectral characteristics:
Infrared: 1500, 1595, 1625 cm$^{-1}$ vC=C vC=N 1640 cm$^{-1}$ vCO
STEP C: 2-Methyl-9-(2-morpholinoethyl)-3-(4-chlorobenzoyl) imidazo[1,2-a]benzimidazole dihydrochloride
1.7 g of the base obtained in Step B is dissolved in 30 ml of acetone and acidified with concentrated hydrochloric acid: the title compound precipitate is removed by filtration and recrystallised from ethanol.
Yield: 89%
Melting point: 235°–236° C.
Percentage composition:
Calculated: C 55.7 H 5.1 Cl 21.5 N 11.3
Found: C 55.4 H 5.1 Cl 21.1 N 11.4

EXAMPLE 40

2-METHYL-9-(2-PIPERIDINOETHYL)-3-(2-FUROYL)-IMIDAZO[1,2-a]BENZIMIDAZOLE DIHYDROCHLORIDE
The title compound is obtained by proceeding in the same manner as in Example 39 but replacing the 4-chlorophenacyl bromide in Step A with 2-furoylmethyl bromide, and the 2-amino-1-(2-morpholinoethyl)benzimidazole with 2-amino-1-(2-piperidinoethyl)benzimidazole.
Melting point: 227°–228° C.
Percentage composition:
Calculated: C 58.8 H 5.8 Cl 15.8 N 12.5
Found: C 58.6 H 5.7 Cl 15.5 N 12.7
Spectral characteristics:
Infrared: 1495, 1600, 1610 cm$^{-1}$ vC=C vC=N 1625 cm$^{-1}$ vCO

EXAMPLE 41

2-METHYL-9-(2-PIPERIDINOETHYL)-3-(2-THENOYL)-IMIDAZO[1,2-a]BENZIMIDAZOLE DIHYDROCHLORIDE
STEP A: 2-amino-1-(2-piperidinoethyl)-3-(2-thenoylmethyl) benzimidazolium bromide
An ethereal solution of 2-bromoacetylthiophene (obtained by brominating 2-acetylthiophene (1.9 g, 15 mmol) with 0.8 ml (15 mmol) of bromine in 10 ml of dioxane and 15 ml of ether) is added to a hot solution of 2-amino-1-(2-piperidinoethyl)benzimidazole (2.44 g; 10 mmol) in 100 ml of acetone. Stir and maintain at room temperature. The next day, the title compound precipitate is collected by means of filtration and washed with acetone and with ether.
Yield: 94%
Melting point: 198° C. (decomposition)
Percentage composition:
Calculated: C 53.3 H 5.6 Br 17.6 N 12.5 S 7.2
Found: C 53.5 H 5.6 Br 17.4 N 12.3 S 7.0
Spectral characteristics
Infrared: 1685 cm$^{-1}$ vC=O 1675 cm$^{-1}$ vC=N 3210, 3340 cm$^{-1}$ vNH$_2$
STEP B: 2-Methyl-9-(2-piperidinoethyl)-3-(2-thenoyl)imidazo [1,2-a]benzimidazole
The bromide obtained in Step A is heated at reflux in 15 ml of acetic anhydride until completely dissolved. Cool and pour into 50 ml of cold water. Neutralise with a solution of sodium carbonate and extract twice with 10 ml of chloroform each time. Combine the organic phases, pass over a column of alumina and evaporate. Recrystallise the residue from ethyl acetate.
Yield: 92%
Melting point: 125°–126° C. (decomposition)
Percentage Composition:
Calculated: C 67.5 H 6.2 N 14.3 S 8.2
Found: C 67.6 H 6.4 N 14.3 S 8.0
Spectral characteristics:
Infrared: 1510, 1590, 1605 cm$^{-1}$ vC=C vC=N 1625 cm$^{-1}$ vCO
STEP C: 2-Methyl-9-(2-piperidinoethyl)-3-(2-thenoyl)-imidazo [1,2-a]benzimidazole dihydrochloride
Dissolve 4 mmol of the compound obtained in the preceding Step in 20 ml of acetone. Acidify with concentrated hydrochloric acid. Filter and recrystallise from ethanol.
Yield: 87%
Melting point: 232° C. (decomposition)
Percentage composition:
Calculated: C 56.8 H 5.6 Cl 15.2 N 12.0 S 6.9
Found: C 56.3 H 5.5 Cl 15.6 N 12.2 S 7.0

EXAMPLE 42

2-METHYL-9-(2-PIPERIDINOETHYL)-3-(2-THENOYL)-IMIDAZO[1,2-a]BENZIMIDAZOLE SULFATE
The title compound is obtained by proceeding as in Example 41 but replacing the hydrochloric acid in Step C with sulfuric acid.
Melting point: 240°–241° C. (decomposition)
Percentage composition:
Calculated: C 53.9 H 5.3 N 11.4
Found: C 53.8 H 5.3 N 11.3

EXAMPLE 43

2-METHYL-9-(2-MORPHOLINOETHYL)-3-(5-BROMO-2-THENOYL)-IMIDAZO [1,2-a]BENZIMIDAZOLE DIHYDROCHLORIDE
The title compound is obtained by proceeding as in Example 41 but in Step A replacing
2-acetylthiophene with 2-acetyl-5-bromothiophene
2-amino-1-(2-piperidinoethyl)benzimidazole with 2-amino-1-(2-morpholinoethyl)benzimidazole.
Melting point: 249° C. (decomposition)
Percentage composition:
Calculated: C 46.2 H 4.2 Br 14.6 Cl 13.0 N 10.3 S 5.9
Found: C 46.5 H 4.4 Br 14.4 Cl 13.0 N 10.2 S 6.0
Spectral characteristics:
Infrared: 1500, 1600, 1610 cm$^{-1}$ vC=C vC=N 1625 cm$^{-1}$ vCO

EXAMPLE 44

2-TERT-BUTYL-1-(2-MORPHOLINOETHYL)IMIDAZO[1,2-a]BENZIMIDAZOLE DIHYDROCHLORIDE

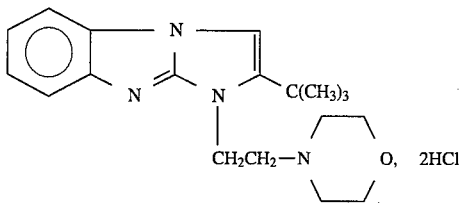

STEP A: 2-(2-Hydroxyethylamino)-1-pivaloylmethylbenzimidazole hydrobromide

Heat at reflux for 3 hours a mixture of 2-(2-hydroxyethylamino)benzimidazole (1.77 g, 10 mmol) and bromopinacoline (1.35 g, 10 mmol) in 50 ml of propanol. Subsequently maintain at room temperature. The next day, the title compound is collected by filtration and washed with acetone and then with ether.
Yield: 89%
Melting point: 212°–213° C. (decomposition)
Percentage composition:
Calculated: C 50.6 H 6.2 Br 22.1 N 11.8
Found: C 50.5 H 6.5 Br 22.0 N 11.7
Spectral characteristics
Infrared: 1720 cm$^{-1}$ $\nu$C=O 3285, 3365 cm$^{-1}$ $\nu$OH $\nu$NH STEP B: 2-tert-butyl-1-(2-hydroxyethyl)imidazo[1,2-a]benzimidazole The hydrobromide obtained in the preceding Step is placed in a receptacle at 225° C. for 10 minutes. The product obtained is treated with ammonium hydroxide and extracted three times with 5 ml of chloroform each time. The organic phases are combined, concentrated and passed over a column of alumina eluted with chloroform. The oil obtained after evaporation is crystallised by trituration in petroleum ether.
Yield: 70%
Melting point: 157°–158° C.
Percentage composition:
Calculated: C 70.3 H 7.6 N 16.1
Found: C 70.2 H 7.5 N 16.3
Spectral characteristics:
Infrared: 1640 cm$^{-1}$ $\nu$C=N 3065, 3205 cm$^{-1}$ $\nu$OH associated STEP C: 2-tert-Butyl-1-(2-chloroethyl)imidazo[1,2-a]benzimidazole hydrochloride Add 0.93 ml of thionyl chloride to a suspension of 1.85 g (7.1 mmol) of the compound obtained in Step B in 20 ml of chloroform while stirring vigorously. Heat at reflux for two hours and cool. Evaporate and triturate the residue in petroleum ether. The precipitate obtained is collected by filtration and washed with petroleum ether.
Yield: 100%
Melting point: 200°–201° C. (decomposition)
Percentage composition:
Calculated: C 57.7 H 6.1 Cl 22.7 N 13.5
Found: C 57.9 H 6.0 Cl 22.5 N 13.6
Spectral characteristics:
Infrared: 1520, 1620 cm$^{-1}$ $\nu$C=C 2300, 2800 cm$^{-1}$ $\nu$–N+H STEP D: 2-tert-Butyl-1-(2-morpholinoethyl)-imidazo[1,2-a]benzimidazole Heat 1 g (3.2 mmol) of the compound obtained in the preceding Step at the boil for 6 hours in 5 ml of morpholine. Cool, then pour into 10 ml of water. Extract three times with chloroform. Combine the organic phases, wash with water and pass over a column of alumina eluted with chloroform. Evaporate the solvent. The title compound is obtained.
Yield: 89%
Percentage composition:
Calculated: C 69.9 H 8.0 N 17.2
Found: C 70.0 H 7.8 N 17.4
Spectral characteristics: $^1$H NMR
$\delta$=1.41 ppm, singlet, 9H, C(CH$_3$)$_3$
$\delta$=1.50 ppm, triplet, 4H, (CH$_2$)$_2$N
$\delta$=2.86 ppm, triplet, 2H, CH$_2$-morpholine
$\delta$=3.63 ppm, triplet, 4H, (CH$_2$)$_2$O
$\delta$=4.28 ppm, triplet, 2H, CH$_2$CH$_2$-morpholine STEP E: 2-tert-butyl-1-(2-morpholinoethyl)-imidazo[1,2-a]benzimidazole dihydrochloride The oil obtained in Step D is dissolved in 15 ml of acetone and the solution obtained is acidified with ethereal hydrogen chloride. Filter the precipitate obtained. Wash with acetone and dry.
Yield: 85%
Melting point: 288° C. (decomposition)
Percentage composition:
Calculated C 57.1 H 7.1 Cl 17.8 N 14.0
Found: C 57.3 H 7.2 Cl 17.5 N 13.8
Spectral characteristics:
Infrared: 1665 cm$^{-1}$ $\nu$C=N$^+$ 2200–2700, 3300–3450 cm$^{-1}$ $\nu$NH$^+$

EXAMPLE 45

2-TERT-BUTYL-1-(2-PIPERIDINOETHYL)-IMIDAZO[1,2-a]BENZIMIDAZOLE DIHYDROCHLORIDE

The title compound is obtained by proceeding as in Example 44 but replacing the morpholine in Step D with piperidine.
Melting point: 231° C. (decomposition)
Percentage composition:
Calculated: C 60.4 H 7.6 Cl 17.8 N 14.1
Found: C 60.6 H 7.9 Cl 17.5 N 14.0
Spectral characteristics
Infrared: 1660 cm$^{-1}$ $\nu$C=N$^+$ 2200–2700, 3300–3450 cm$^{-1}$ $\nu$NH$^+$

EXAMPLE 46

2-TERT-BUTYL-1-(2-N,N-DIETHYLAMINOETHYL)-IMIDAZO[1,2-a]BENZIMIDAZOLE DIHYDROCHLORIDE

The title compound is obtained by proceeding as in Example 44 but replacing the morpholine in Step D with N,N-diethylamine.
Melting point (hydrate): 240°–241° C. (decomposition)
Percentage composition:
Calculated: C 56.6 H 8.0 Cl 17.6 N 13.9
Found: C 56.6 H 7.8 Cl 17.3 N 14.0
Spectral characteristics: $^1$H NMR (CDCl$_3$) base
$\delta$=0.72 ppm, triplet, 6H, 2 CH$_3$
$\delta$=1.41 ppm, singlet, 9H, C(CH$_3$)$_3$
$\delta$=2.35 ppm, quadruplet, 4H, N(CH$_2$)$_2$
$\delta$=2.76 ppm, triplet, 2H, CH$_2$—N(Et)$_2$
$\delta$=4.18 ppm, triplet, 2H, CH$_2$—CH$_2$—N(Et)$_2$
$\delta$=6.9 ppm, singlet, 1H, imidazole
$\delta$=7.12–7.45 ppm, unresolved peaks, 4H, aromatic

EXAMPLE 47

10-(2-DIETHYLAMINOETHYL)-2,3,4,10-TETRAHYDROPYRIMIDINO[1,2-a]BENZIMIDAZOLE DIHYDROCHLORIDE

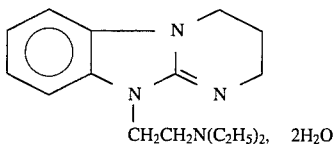

CH₂CH₂N(C₂H₅)₂, 2H₂O

STEP A: 10-(2-Diethylaminoethyl)-2,3,4,10-tetrahydropyrimidino[1,2-a]benzimidazole Heat at reflux for five hours a mixture of 2.32 g (10 mmol) of 2-amino-1-diethylaminoethyl benzimidazole and 1.2 ml (10 mmol) of 1-bromo-3-chloropropane in 10 ml of xylene. Add 50 ml of water and stir until a solution is obtained. Separate the aqueous phase, render alkaline with ammonium hydroxide to a pH of 9, and extract three times with chloroform. Combine the organic phases, concentrate and elute with chloroform on a column of alumina. Collect the first fraction and evaporate the solvent. Dry.
Yield: 86%
Percentage composition:
Calculated: C 66.2 H 9.0 N 19.3
Found: C 66.0 H 9.3 N 19.5
Spectral characteristics:
Infrared: 1660 cm$^{-1}$ νC=N STEP B: 10-(2-diethylaminoethyl)-2,3,4,10-tetrahydropyrimidino[1,2-a]benzimidazoledihydrochloride (dihydrate)

The base obtained in the preceding Step is dissolved in 20 ml of ether and the solution is acidified with ethereal hydrogen chloride. Filter the precipitate obtained, wash with ether and dry.
Yield: 91.6%
Melting point: 78°–80° C. (decomposition)
Percentage composition (dihydrate):
Calculated: C 50.4 H 7.9 Cl 18.6 N 14.7
Found: C 50.1 H 8.2 Cl 18.4 N 14.5

EXAMPLE 48

10-PHENACYL-2,3,4,10-TETRAHYDROPYRIMIDINO[1,2-a]BENZIMIDAZOLE HYDROCHLORIDE

STEP A: 2-(3-Hydroxypropylamino)benzimidazole

Heat at 145°–150° C. for two hours a mixture of 5 g (25 mmol) of 2-benzimidazolesulfonic acid and 5.7 ml (75 mmol) of 3-aminopropanol. Cool to 90° C. and add 15 ml of cold water, with vigorous stirring, until a precipitate is formed. Maintain at a temperature of approximately 4° C. for one night, filter the title compound precipitate, wash with cold water and dry.
Yield: 95%
Melting point: 139°–140° C.
Percentage composition:
Calculated: C 62.8 H 6.9 N 22.0
Found: C 62.6 H 6.9 N 22.3
Spectral characteristics:
Infrared: 1500, 1580, 1600 cm$^{-1}$ νC=C 1650 cm$^{-1}$ νC=N 3070–3240 cm$^{-1}$ νOH νNH STEP B: 2-(3-Hydroxypropylamino)-1-phenacylbenzimidazole hydrobromide Heat at reflux for 5 to 6 hours a mixture of 1.91 g (10 mmol) of the compound obtained in Step A and 1.99 g (10 mmol) of phenacyl bromide in 20 ml of isopropanol. Cool. Collect the title compound precipitate by filtration and wash with acetone. Recrystallise from ethanol.
Yield: 82%
Melting point: 237°–238° C.
Percentage composition:
Calculated: C 55.4 H 5.2 Br 20.5 N 10.8
Found: C 55.6 H 5.1 Br 20.0 N 10.5
Spectral characteristics:
Infrared: 1700 cm$^{-1}$ νCO 1650 cm$^{-1}$ νC=N 3100–3240 cm$^{-1}$ νOH νNH STEP C: 10-Phenacyl-2,3,4,10-tetrahydropyrimidino[1,2-a]benzimidazole With stirring, slowly add 0.7 ml (10 mmol) of thionyl chloride to a suspension of 1.95 g (5 mmol) of the compound obtained in Step B in 25 ml of chloroform. Heat at reflux until the starting material and its chlorinated derivative have disappeared (monitored by thin-layer chromatography). Evaporate the reaction mixture, treat the residue with ammonium hydroxide and extract three times with chloroform. Combine the organic phases, evaporate, and heat the residue at 110°–120° C. for 20 minutes; treat with ammonium hydroxide and with chloroform. The chloroform phase is passed over a column of alumina eluted with chloroform. Collect the fraction $R_f$–0.3. Evaporate the solvent and recrystallise the title compound from acetonitrile.
Yield: 86.2%
Melting point: 168°–169° C. (decomposition)
Percentage composition:
Calculated: C 74.2 H 5.9 N 14.4
Found: C 74.2 H 5.7 N 14.2
Spectral characteristics
Infrared: 1505, 1590, 1605 cm$^{-1}$ νC=C 1660 cm$^{-1}$ νC=N 1690 cm$^{-1}$ νC=O
$^1$H NMR (CDCl₃): base
δ=1.89 ppm, unresolved peaks, 2H, CH₂(3)
δ=3.45 ppm, triplet, 2H, N—CH₂ (4)
δ=3.75 ppm, triplet, 2H, N—CH₂ (2)
δ=5.10 ppm, singlet, 2H, CH₂—CO
δ=6.80 ppm, unresolved peaks, 9H, aromatic STEP D: 10-Phenacyl-2,3,4,10-tetrahydropyrimidino[1,2-a]benzimidazole hydrochloride The compound obtained in Step C is dissolved in acetone. The solution obtained is treated with concentrated hydrochloric acid. Suction-filter the precipitate and recrystallise from ethanol.
Melting point: 288°–289° C.
Percentage composition:
Calculated: C 66.0 H 5.5 Cl 10.8 N 12.8
Found: C 65.7 H 5.7 Cl 11.0 N 12.5
Spectral characteristics:
Infrared: 1670 cm$^{-1}$ ν(C=N⁺—H) 1700 cm$^{-1}$ ν(C=O)

EXAMPLE 49

10-PHENACYL-2,3,4,10-TETRAHYDROPYRIMIDINO[1,2-a]BENZIMIDAZOLE

STEP A: [1H]-1,2,3,4-tetrahydropyrimidino[1,2-a]benzimidazole

Add a solution of thionyl chloride in dimethylformamide dropwise, at room temperature, to a solution obtained by heating 2-(3-hydroxypropylamino)benzimidazole (obtained in Example 48, Step A) in dimethylformamide. Subsequently, heat at reflux for four hours, cool, dilute with water and neutralise with ammonium hydroxide. Thirty minutes later, separate the title compound, wash with water and recrystallise from acetonitrile.
Yield: 82%
Melting point: 210°–211° C.

Percentage composition:
Calculated: C 69.4 H 6.5 N 24.1
Found: C 69.3 H 6.4 N 24.3
Spectral characteristics:
Infrared: 1620 cm$^{-1}$ νCN
$^1$H NMR (CDCl$_3$):
δ=2.12 ppm, triplet, 2H, CH$_2$ (3)
δ=3.47 ppm, triplet, 2H, CH$_2$ (4)
δ=3.91 ppm, triplet, 2H, CH$_2$ (2)
δ=6.95–7.20 ppm, 5H, aromatic STEP B: 10-Phenacyl-2,3,4,10-tetrahydropyrimidino[1,2-a]benzimidazole 1.38 g (8 mmol) of the compound obtained in Step A is dissolved in 50 ml of xylene at 120° C. Cool to 50° C. and add 1.59 g (8 mmol) of phenacyl bromide. Stir vigorously until dissolved, then heat at the boil and leave at reflux for one hour. Cool, separate the precipitate formed, wash with petroleum ether, dry and treat with ammonium hydroxide. Separate the title compound precipitate and recrystallise from acetonitrile.
Yield: 95%
Melting point: 168°–169° C. (decomposition)

EXAMPLE 50

10-(4'-CHLOROPHENACYL)-2,3,4,10-TETRAHYDROPYRIMIDINO[1,2-a]BENZIMIDAZOLE HYDROCHLORIDE

The title compound is obtained by proceeding as in Examples 48 and 49 but replacing the phenacyl bromide in Steps B with 4-chlorophenacyl bromide.
Melting point: 270°–271° C.
Percentage composition:
Calculated: C 59.7 H 4.7 Cl 19.6 N 11.6
Found: C 59.5 H 4.5 Cl 19.3 N 11.5
Spectral characteristics:
Infrared: 1670 cm$^{-1}$ νC=N$^+$ 1700 cm$^{-1}$ νC=O
$^1$H NMR (CDCl$_3$):
δ=1.89 ppm, unresolved peaks, 2H, CH$_2$ (3)
δ=3.45 ppm, unresolved peaks, 2H, CH$_2$ (4)
δ=3.75 ppm, unresolved peaks, 2H, CH$_2$ (2)
δ=5.20 ppm, singlet, 2H, CH$_2$—CO

EXAMPLE 51

10-(4'-METHOXYPHENACYL)-2,3,4,10-TETRAHYDROPYRIMIDINO[1,2-a]BENZIMIDAZOLE HYDROCHLORIDE

The title compound is obtained by proceeding as in Steps B with 4-methoxyphenacyl bromide.
Melting point: 260°–262° C. (decomposition)
Percentage composition:
Calculated: C 63.8 H 5.6 Cl 9.9 N 11.7
Found: C 63.9 H 5.5 Cl 10.1 N 11.5
Spectral characteristics:
Infrared: 1670 cm$^{-1}$ νC=N$^+$H 1690 cm$^{-1}$ νCO
$^1$H NMR (CDCl$_3$):
δ=1.89 ppm, quintuplet, 2H, CH$_2$ (3)
δ=3.48 ppm, triplet, 2H, CH$_2$ (4)
δ=3.25 ppm, triplet, 2H, CH$_2$ (2)
δ=3.78 ppm, singlet, 3H, OCH$_3$
δ=5.10 ppm, singlet, 2H, CH$_2$—CO

EXAMPLE 52

10-[2-HYDROXY-2-(4-CHLOROPHENYL)ETHYL]-2,3,4,10-TETRAHYDROPYRIMIDINO[1,2-a]BENZIMIDAZOLE HYDROCHLORIDE

STEP A: 10-[2-Hydroxy-2-(4-chlorophenyl)ethyl]-2,3,4,10-tetrahydropyrimidino[1,2-a]benzimidazole Add 0.35 g (9.3 mmol) of sodium borohydride in small portions, with vigorous stirring, to a suspension of 3.0 g (9.3 mmol) of 10-(4-chlorophenacyl)-2,3,4,10-tetrahydropyrimidino[1,2-a]benzimidazole (obtained in Example 50) in 20 ml of ethanol. Maintain stirring for one hour and leave for 12 hours at room temperature. Acidify with hydrochloric acid, and evaporate the reaction mixture. Treat the residue with ammonium hydroxide and extract with chloroform. The organic phase obtained is passed over a column of alumina. Evaporate the solvent. The residue is the title compound.
Melting point: 146°–147° C.
Percentage composition:
Calculated: C 65.9 H 5.5 Cl 10.8 N 12.8
Found: C 65.6 H 5.7 Cl 10.5 N 12.5
Spectral characteristics:
Infrared: 1490, 1600 cm$^{-1}$ νC=C 1650 cm$^{-1}$ νCDCl$_3$
$^1$H NMR (CDCl$_3$):
δ=1.91 ppm, quintet, 2H, CH$_2$ (3)
δ=3.51 ppm, triplet, 2H, CH$_2$ (4)
δ=3.74 ppm, triplet, 2H, CH$_2$ (2)
δ=3.94 ppm, triplet, 1H, CH
δ=5.00 ppm, doublet, 2H, CH$_2$—CH STEP B: 10-[2-Hydroxy-2-(4-chlorophenyl)ethyl]-2,3,4,10-tetrahydropyrimidino[1,2-a]benzimidazole hydrochloride Slowly add isopropanolic hydrogen chloride to an isopropanol solution of the base obtained in Step A. Wait for 30 minutes. Suction-filter, and wash with acetone.
Yield: 90%
Melting point: 253°–254° C. (decomposition)
Percentage composition:
Calculated: C 59.3 H 5.3 Cl 19.5 N 11.5
Found: C 59.4 H 5.5 Cl 19.4 N 11.3

EXAMPLE 53

10-[2-HYDROXY-2-(4-METHOXYPHENYL)ETHYL]-2,3,4,10-TETRAHYDROPYRIMIDINO[1,2-a]BENZIMIDAZOLE HYDROCHLORIDE

The title compound is obtained by proceeding as in Example 52 but replacing the 10-(4-chlorophenacyl)-2,3,4,10-tetrahydropyrimidino[1,2-a]benzimidazole in Step A with 10-(4-methoxyphenacyl)-2,3,4,10-tetrahydropyrimidino[1,2-a]benzimidazole obtained in Example 51.
Melting point: 210°–212° C.
Percentage composition:
Calculated: C 63.4 H 6.2 Cl 9.9 N 11.7
Found: C 63.2 H 6.5 Cl 9.5 N 11.9
Spectral characteristics
Infrared: 1500–1610 cm$^{-1}$ νC=C 1640 cm$^{-1}$ νC=N
$^1$NMR (CDCl$_3$):
δ=1.85 ppm, quadruplet, 2H, CH$_2$ (3)
δ=3.87 ppm, triplet, 1H, CH
δ=4.92 ppm, doublet, 2H, CH$_2$CH

EXAMPLE 54

1-(2-DIETHYLAMINOETHYL)-1,2,3,4-TETRAHYDRO-PYRIMIDINO[1,2-a]BENZIMIDAZOLE SULFATE (TRIHYDRATE)

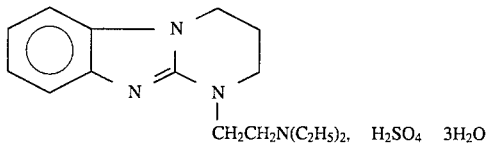

CH₂CH₂N(C₂H₅)₂, H₂SO₄ 3H₂O

STEP A: 1-(2-Diethylaminoethyl)-1,2,3,4-tetrahydropyrimido [1,2-a]benzimidazole
Heat at reflux for 12 hours a mixture of 1.16 g (5 mmol) of 2-(2-diethylaminoethylamino)benzimidazole and 0.6 ml (5 mmol) of 1-bromo-3-chloropropane in 10 ml of xylene. After cooling, the xylene is decanted off and the residual oil is treated with petroleum ether. Evaporate the remaining petroleum ether and treat with ammonium hydroxide. Extract with chloroform. The combined organic phases are concentrated and passed over a column of alumina eluted with chloroform. The evaporation of the solvent allows the title compound to be obtained.
Yield: 42%
Percentage composition:
Calculated: C 70.5 H 8.9 N 20.6
Found: C 70.4 H 9.1 N 20.8
Spectral characteristics:
Infrared: 1625 cm⁻¹ ν(C=N)
¹NMR (CDCl₃)
δ=0.97 ppm, triplet, 6H, (2CH₃)
δ=2.16 ppm, quintuplet, H, CH₂ (3)
δ=2.55 ppm, quadruplet, H, N(CH₂)₂
δ=2.72 ppm, triplet, 2H, CH₂N
δ=3.47 ppm, triplet, 2H, CH₂ (4)
δ=3.66 ppm, triplet, 2H, CH₂ (2)
δ=3.89 ppm, triplet, 2H, NCH₂CH₂N (Et)₂

STEP B: 1-(2-Diethylaminoethyl)-1,2,3,4-tetrahydro pyrimidino[1,2-a]benzimidazole sulfate (trihydrate)
Dissolve the base obtained in Step A in 10 ml of acetone and acidify with sulfuric acetone. Triturate and add acetone in small portions; filter; dry and recrystallise from acetonitrile.
Yield: 98%
Percentage composition (trihydrate):
Calculated: C 45.5 H 7.6 N 13.3 S 7.6
Found: C 45.5 H 7.5 N 13.0 S 7.4

EXAMPLE 55

1-(2-PIPERIDINOETHYL)-1,2,3,4-TETRAHYDROPYRIMIDINO[1,2-a]BENZIMIDAZOLE DIHYDROCHLORIDE (TRIHYDRATE)
The title compound is obtained by proceeding as in Example 54 but replacing the 2-(2-diethylaminoethylamino)benzimidazole in Step A with 2-(2-piperidinoethylamino)benzimidazole and the sulfuric acid in Step B with hydrochloric acid.
Melting point: 188°–190° C. (decomposition)
Percentage composition:
Calculated: C 49.6 H 7.8 Cl 17.2 N 13.6
Found: C 49.6 H 7.9 Cl 16.9 N 13.5
Spectral characteristics
Infrared: 1620 cm⁻¹ νC=N
¹H NMR (CDCl₃):
δ=1.44 ppm, unresolved peaks, 6H, piperidine
δ=2.15 ppm, quintuplet, 2H, CH₂ (3)
δ=2.42 ppm, unresolved peaks, 4H, piperidine
δ=2.63 ppm, triplet, 2H, CH₂—N
δ=3.43 ppm, triplet, 2H, CH₂ (4)
δ=3.68 ppm, triplet, 2H, CH₂ (2)

EXAMPLE 56

1-(2-MORPHOLINOETHYL)-1,2,3,4-TETRAHYDROPYRIMIDINO[1,2-a]BENZIMIDAZOLE DIHYDROCHLORIDE (TRIHYDRATE)

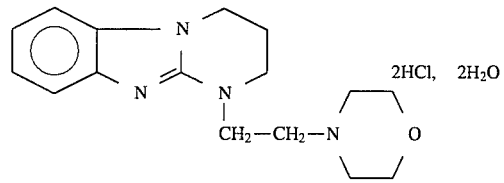

2HCl, 2H₂O

The title compound is obtained by proceeding as in Example 55 but replacing the 2-(2-piperidinoethylamino)benzimidazole with 2-(2-morpholinoethylamino)benzimidazole.
Melting point: 284°–285° C. (decomposition)
Percentage composition:
Calculated: C 48.6 H 7.1 Cl 17.9 N 14.2
Found: C 48.4 H 7.0 Cl 18.0 N 14.2
Spectral characteristics
Infrared: 1620 cm⁻¹ νC=N
¹H NMR (CDCl₃):
δ=2.16 ppm, quintuplet, 2H, CH₂ (3)
δ=2.46 ppm, multiplet, 4H, morpholine N CH₂ (2)
δ=2.63 ppm, triplet, 2H, CH₂-morpholine
δ=3.43 ppm, triplet, 2H, CH₂ (4)
δ=3.65 ppm, unresolved peaks, 6H, morpholine and CH₂ (2)
δ=3.88 ppm, triplet, 2H, CH₂—CH₂-morpholine

EXAMPLE 57

9-[2-HYDROXY-2-(4-METHOXYPHENYL)ETHYL]-2,3-DIHYDROIMIDAZO [1,2-a]BENZIMIDAZOLE HYDROCHLORIDE
Add 0.3 g (7.5 mmol) of sodium borohydride bit by bit to a suspension of 2.41 g (7 mmol) of 9-(4'-methoxyphenacyl)-2,3-dihydroimidazo[1,2-a]benzimidazole—described in Example 6—in 15 ml of methanol over a period of thirty minutes at room temperature. Continue stirring for a further four hours and leave until the next day. Subsequently, add 10 ml of 10% hydrochloric acid until a pH of 2–3 is obtained, and evaporate the methanol. Treat the residue with an ammonium hydroxide solution and extract with chloroform. Recrystallise the residue. The title compound is obtained in the form of a base. Dissolve in hot ethanol and add ethereal hydrogen chloride. Allow to cool, suction-filter, and wash with ether. The title compound is obtained.
Melting point: 192°–193° C.
Percentage composition:
Calculated: C 62.5 H 5.8 Cl 10.3 N 12.1
Found: C 62.6 H 6.0 Cl 10.5 N 12.4
Spectral characteristics:
Infrared: 1660 cm⁻¹ ν(C=N) 3100–3600 cm⁻¹ ν(OH)
Nuclear magnetic resonance: (¹H) (CF₃COOD)
δ=3.5 ppm, singlet, 3H, OCH₃
δ=4.9 ppm, triplet, 2H, CH₂

PHARMACOLOGICAL STUDY OF THE COMPOUNDS OF THE INVENTION

EXAMPLE A

ACUTE TOXICITY STUDY

The acute toxicity was evaluated after the oral administration to groups, each comprising 8 mice (26±2 grams), of increasing doses of the compounds being studied. The animals were observed at regular intervals during the course of the first day, and daily for two weeks, following the treatment. The compounds of the invention appear to be of very low toxicity.

EXAMPLE B
HYPOGLYCAEMIC ACTIVITY STUDY

The hypoglycaemic activity of the compounds of the invention was researched on white rats (160–190 g) using five animals per compound studied; the animals are given a diet of water for eighteen hours before the beginning of the experiment. The compounds to be studied are administered by the intraperitoneal route in a single dose of 50 mg/kg$^{-1}$. The blood glucose concentration is determined by samples taken before injection of the compound and then 2 hours, 4 hours and 6 hours after administration. The dosage was calculated by the fermentation method using Bio-La-test kits (Lachema-Czhekoslovakia). A spectrophotometer KFK-2 ($\lambda$=490 nm) was used for that operation.

The blood glucose concentrations were compared with a standard solution of glucose (10 mmol/l). The compounds of the invention appear to have a hypoglycaemic activity comparable to that of gliclazide. Their duration of action is longer than twelve hours.

EXAMPLE C
PLATELET ANTI-AGGREGATION ACTIVITY STUDY

The platelet anti-aggregation activity study of the compounds of the invention was researched in accordance with the method of G.V.R. BORN (Aggregation of blood platelets by adenosine diphosphate and its reversal—Nature 1962-v. 194 p 927–929). For those experiments, a rabbit plasma rich in platelets containing at least $2.5\times10^8$ platelets per ml was used. ADP (adenosine diphosphate) acts as an inductor. Before using ADP, the compounds of the invention are placed in the presence of the platelet-rich plasma. Each compound was studied on five different specimens of platelet-rich plasma. The platelet aggregation was evaluated as a percentage decrease in the optical density of the platelet-rich plasma by photoelectrocolorimetric recording. The $ID_{50}$ of the compounds of the invention (dose at which platelet aggregation is decreased by half) is less than 10–4M for the compounds of the invention.

EXAMPLE D
ANTIHYPERTENSIVE ACTIVITY RESEARCH

The animals are acclimatised for a period of six days before the beginning of the study. At the beginning of the experiment, the rats are anaesthetised with 1000 mg/kg$^{-1}$ of urethane administered by the intraperitoneal route. A catheter is introduced into the jugular vein.

A catheter connected to a precision recorder is placed in the carotid artery. A period of 10 minutes is allowed to pass to allow the arterial pressure to stabilize before taking the first measurement.

In a first period, the solvent is administered by the intravenous route to all the animals, the arterial pressure is recorded for a period of 30 minutes after the administration, and readings of the arterial pressure are taken 10, 20 and 30 minutes after the administration. The compounds of the invention are administered in saline solution also by the intravenous route. The recording of the arterial pressure is carried out for a period of 30 minutes and pressure readings are taken 10, 20 and 30 minutes after the administration. The compounds of the invention do not bring about any significant decrease in arterial pressure.

EXAMPLE E
PHARMACEUTICAL COMPOSITION

Tablets designed for the treatment of diabetes and its complications comprising 20 mg of 9-(2-diethylaminoethyl)-2,3-dihydroimidazo[1,2-a]benzimidazole dihydrochloride.

| Formulation for 1000 tablets: | |
| --- | --- |
| 9-(2-diethylaminoethyl)-2,3-dihydroimidazo-[1,2-a]benzimidazole dihydrochloride | 20 g |
| wheat starch | 15 g |
| lactose | 65 g |
| magnesium stearate | 2 g |
| silica | 1 g |
| hydroxypropylcellulose | 2 g |

We claim:

1. A compound selected from those of the general formula (I):

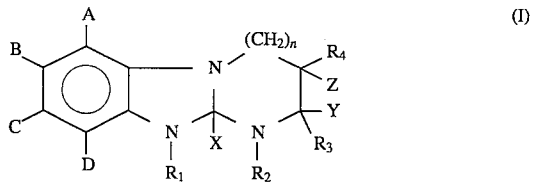

wherein:
either:

I.
n=0, the third ring being 5-membered,

A, B, C and D, which are the same or different, each represents hydrogen, halogen, lower alkyl, lower alkoxy, hydroxy, trifluoromethyl, or hydroxy-lower alkyl, Y and Z each represents hydrogen or together form a bond, and either:

I.A.
X and $R_2$ together form a bond and in that case:

I.A.1
$R_1$ represents a $G_1$ group,
$G_1$ representing the group

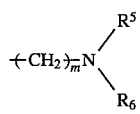

wherein m represents an integer of 1 to 6 inclusive and $R_5$ and $R_6$, which are the same or different:

a/ each represents, independently of the other, hydrogen, lower alkyl, aryl-lower alkyl or substituted aryl-lower alkyl, and $R_3$ represents hydrogen, lower alkyl, phenyl substituted by hydroxy, hydroxyalkyl, or by two to five groups selected from lower alkyl, lower alkoxy, trifluoromethyl, hydroxy, and hydroxyalkyl, or $R_3$ represents naphthyl, substituted naphthyl, heteroaryl, substituted heteroaryl, or group $G_1$, $G_1$ being as defined hereinbefore, b/ or $R_5$ and $R_6$ together with the nitrogen atom that carries them form a morpholine ring, and $R_3$ represents hydrogen, lower alkyl, phenyl substituted by lower alkyl, hydroxy, halogen, trifluoromethyl, or by hydroxyalkyl, or by two to five groups selected from lower alkyl, lower alkoxy, halogen, trifluoromethyl, hydroxy, and hydroxyalkyl, or $R_3$ represents naphthyl, substituted naphthyl, heteroaryl group, substituted heteroaryl, or group $G_1$, $G_1$ being as defined hereinbefore, c/ or $R_5$ and $R_6$ together with the nitrogen atom that carries them form piperazine, which is optionally substituted at the nitrogen atom in the 4-position by lower alkyl, aryl, aryl-lower alkyl, substituted aryl, or substituted aryl-lower alkyl, and $R_3$ represents lower alkyl, phenyl substituted by hydroxy, halogen, trifluoromethyl, or by hydroxyalkyl, or by two to five groups selected from lower alkyl, lower alkoxy, halogen, trifluoromethyl, hydroxy, and hydroxyalkyl, or $R_3$ represents naphthyl, substituted naphthyl, heteroaryl, or substituted heteroaryl;

or $R_1$ represents $G_2$, $G_2$ denoting $(CH_2)_m COR_7$, or $G_3$, $G_3$ denoting $(CH_2)_m CHOHR_7$, wherein m is as defined hereinbefore and $R_7$ represents aryl or substituted aryl, and $R_3$ represents hydrogen, lower alkyl, phenyl substituted by hydroxy, hydroxyalkyl, or by lower alkoxy, lower alkyl, or by two to five groups selected from lower alkyl, lower alkoxy, trifluoromethyl halogen, hydroxy, and hydroxyalkyl, or $R_3$ represents naphthyl, substituted naphthyl, heteroaryl, substituted heteroaryl, or $G_1$, $G_1$ being as defined hereinbefore, $R_4$ represents hydrogen, a group $G_1$ with $G_1$ being as defined hereinbefore, a group $G_4$, of the formula:

$$-COO-G_1$$

wherein $G_1$ is as defined hereinbefore, or a group $G_5$, of the formula $COR_9$, wherein $R_9$ represents aryl, substituted aryl, heteroaryl, or substituted heteroaryl, with the exception of compounds in which $R_4$ represents hydrogen at the same time as $R_1$ represents a group:

$$(CH_2)_m - N\begin{matrix}R_5\\R_6\end{matrix}$$

wherein m=2 and $R_5$ and $R_6$ each represents ethyl whilst at the same time $R_3$ represents lower alkyl or naphthyl,

I.A.2

X and $R_2$ together form a bond and $R_1$ represents a group $G_6$ of the formula $(CH_2)_m R_8$, m being as defined hereinbefore and $R_8$ representing lower alkyl, phenyl, substituted phenyl, naphthyl, or substituted naphthyl, and $R_3$ represents lower alkyl, aryl, substituted aryl, heteroaryl, substituted heteroaryl, hydrogen, or a group $G_1$, $G_1$ being as defined hereinbefore, and $R_4$ represents a $G_1$, $G_4$ or $G_5$ group, $G_1$, $G_4$ and $G_5$ being as defined hereinbefore, or

I.A.3

X and $R_2$ together form a bond and $R_1$ represents methyl, and $R_3$ represents lower alkyl, aryl, substituted aryl, heteroaryl, substituted heteroaryl, hydrogen, or $G_1$, $G_1$ being as defined hereinbefore, and $R_4$ represents $G_4$, $G_4$ being as defined hereinbefore, or $G_7$, $G_7$ denoting the group $COR_{10}$ wherein $R_{10}$ represents naphthyl, substituted naphthyl, substituted phenyl, heteroaryl, or substituted heteroaryl, or

I.B

X and $R_1$ together form a bond, and $R_2$ represents:

$G_1$, $G_1$ being as defined hereinbefore, and $R_3$ represents substituted phenyl, naphthyl, substituted naphthyl, heteroaryl, substituted heteroaryl, or $G_1$, $G_1$ being as defined hereinbefore, whilst $R_4$ represents hydrogen or a group $G_1$, $G_4$ or $G_5$, $G_1$, $G_4$ and $G_5$ being as defined hereinbefore, or $R_2$ represents $G_2$ or a group $G_3$, $G_2$ and $G_3$ being as defined hereinbefore, and $R_3$ represents hydrogen, lower alkyl, aryl, substituted aryl, heteroaryl, substituted heteroaryl, or $G_1$, $G_1$ being as defined hereinbefore, whilst $R_4$ represents hydrogen or a group $G_1$, $G_4$ or $G_5$, $G_1$, $G_4$ and $G_5$ being as defined hereinbefore, or

II.

n=1, the third ring being 6-membered, and

A, B, C and D, which are the same or different, each represents hydrogen, halogen, lower alkyl, or trifluoromethyl, X and $R_2$ form a bond or X and $R_1$ form a bond, wherein at least one of those two bonds must be present in the molecule, Y and Z each represents hydrogen or together form a bond, $R_1$ or $R_2$—depending on whether X and $R_2$ or X and $R_1$ form a bond—represents methyl or $G_1$ or $G_2$ or $G_3$ or $G_6$, $G_1$, $G_2$, $G_3$ and $G_6$, each being as defined hereinbefore, $R_3$ represents hydrogen, lower alkyl, aryl, substituted aryl, heteroaryl, substituted heteroaryl, or a group $G_1$, $G_1$ being as defined hereinbefore, and $R_4$ represents hydrogen or $G_1$, or $G_4$, or $G_5$, with $G_1$, $G_4$ and $G_5$ being as defined hereinbefore, their stereoisomers, as well as their addition salts with a pharmaceutically-acceptable acid, it being understood by lower alkyl or lower alkoxy a straight-chain or branched group containing 1 to 6 carbon atoms, inclusive it being understood that aryl means phenyl or naphthyl, and that heteroaryl means furyl, thienyl, pyridyl, pyrrolyl, imidazolyl, benzimidazolyl, benzofuryl, benzothienyl, quinolyl, isoquinolyl, or indolyl, the term "substituted" qualifying the terms arylalkyl, aryl, phenyl, naphthyl, and heteroaryl indicating, unless specified otherwise, that the groups in question are substituted in the cyclic moiety by one to three radicals selected from halogen, trifluoromethyl, hydroxy, lower alkoxy, hydroxy-lower alkyl, and lower alkyl, and that if there exist in one molecule several $G_1$ groups or $R_5$ and $R_6$ groups, those may be the same or different.

2. Compound according to claim 1, wherein n is 0, X and $R_2$ form a bond, and Z and Y each represents hydrogen, its stereoisomers and also, where appropriate, its addition salts with a pharmaceutically-acceptable acid.

3. A compound according to claim 1, wherein n is 0, and X and $R_2$ and Y and Z form a bond, its stereoisomers, and also its addition salts with a pharmaceutically-acceptable acid form a bond.

4. A compound according to claim 1, wherein $R_4$ represents hydrogen, its stereoisomers, and also its addition salts with a pharmaceutically-acceptable acid.

5. A compound according to claim 1, wherein n is 1, Y and Z each represents hydrogen, and X and $R_2$ together form a bond, its stereoisomers, and also its addition salts with a pharmaceutically-acceptable acid.

6. A compound according to claim 1, wherein n is 1, Y and Z each represents hydrogen, and $R_1$ and X together form a bond, its stereoisomers, and also its addition salts with a pharmaceutically-acceptable acid.

7. A compound according to claim 1, wherein n is 0, Y and Z together form a bond, and X and $R_1$ together form a bond, its stereoisomers, and also its addition salts with a pharmaceutically-acceptable acid.

8. A compound according to claim 1, selected from 9-(2-diethylaminoethyl)-2,3-dihydroimidazo[1,2-a]benzimidazole, its stereoisomers and also their addition salts with a pharmaceutically-acceptable acid.

9. A compound according to claim 1 selected from the group consisting of:
9-MORPHOLINOETHYL-2,3-DIHYDROIMIDAZO[1,2-a]BENZIMIDAZOLE
9-PHENACYL-2,3-DIHYDROIMIDAZO[1,2-a]BENZIMIDAZOLE
9-(p-CHLOROPHENACYL)-2,3-DIHYDROIMIDAZO[1,2-a]BENZIMIDAZOLE
9-(p-METHOXYPHENACYL)-2,3-DIHYDROIMIDAZO[1,2-a]BENZIMIDAZOLE
9-(1-NAPHTHOYLMETHYL)-2,3-DIHYDROIMIDAZO[1,2-a]BENZIMIDAZOLE
9-(2-HYDROXY-2-PHENYLETHYL)-2,3-DIHYDROIMIDAZO[1,2-a]BENZIMIDAZOLE
9-[2-HYDROXY-2-(4'-CHLOROPHENYL)ETHYL]-2,3-DIHYDROIMIDAZO [1,2-a]BENZIMIDAZOLE
9-[2-(1-NAPHTHYL)-2-HYDROXYETHYL]-2,3-DIHYDROIMIDAZO[1,2-a]BENZIMIDAZOLE
2-TERT-BUTYL-9-(2-MORPHOLINOETHYL)-IMIDAZO[1,2-a]BENZIMIDAZOLE
2-TERT-BUTYL-9-(3-DIMETHYLAMINOPROPYL)-IMIDAZO[1,2-a]BENZIMIDAZOLE
9-(2-MORPHOLINOETHYL)-2-(4-HYDROXYPHENYL)-IMIDAZO[1,2-a]BENZIMIDAZOLE
9-(2-MORPHOLINOETHYL)-2-(3-HYDROXYPHENYL)-IMIDAZO[1,2-a]BENZIMIDAZOLE
9-(DIETHYLAMINOETHYL-2-(3,4-DIMETHOXYPHENYL)-IMIDAZO[1,2-a]BENZIMIDAZOLE
9-DIETHYLAMINOETHYL-2-(3,4-DIHYDROXYPHENYL)-IMIDAZO[1,2-a]BENZIMIDAZOLE
9-(2-DIETHYLAMINOETHYL)-2-(1-METHYL-2-BENZIMIDAZOLYL)-IMIDAZO [1,2-a]BENZIMIDAZOLE
9-(2-DIETHYLAMINOETHYL)-2-(2-THIENYL)-IMIDAZO[1,2-a]BENZIMIDAZOLE
2-(5-BROMO-2-THIENYL)-9-(2-MORPHOLINOETHYL)-IMIDAZO[1,2-a]BENZIMIDAZOLE
2-(2-FURYL)-9-(2-N,N-DIETHYLAMINOETHYL)-IMIDAZO[1,2-a]BENZIMIDAZOLE
2-(2-FURYL)-9-(2-MORPHOLINOETHYL)-IMIDAZO[1,2-a]BENZIMIDAZOLE
9-BENZYL-2-DIETHYLAMINOMETHYLIMIDAZO[1,2-a]BENZIMIDAZOLE
2,9-DIMETHYL-3-(v-DIMETHYLAMINOPROPOXYCARBONYL)-IMIDAZO[1,2-a]BENZIMIDAZOLE
3-DIETHYLAMINOMETHYL-2,6,7-TRIMETHYL-9-ETHYLIMIDAZO[1,2-a]BENZIMIDAZOLE
3-DIMETHYLAMINOMETHYL-2-PHENYL-9-ETHYLIMIDAZO[1,2-a]BENZIMIDAZOLE
3-PIPERIDINOMETHYL-2-PHENYL-9-ETHYLIMIDAZO[1,2-a]BENZIMIDAZOLE
2-METHYL-9-(2-MORPHOLINOETHYL)-3-(4-CHLOROBENZOYL)-IMIDAZO [1,2-a]BENZIMIDAZOLE
2-METHYL-9-(2-MORPHOLINOETHYL)-3-(5-BROMO-2-THENOYL)-IMIDAZO[1,2-a]BENZIMIDAZOLE
2-TERT-BUTYL-1-(2-MORPHOLINOETHYL)-IMIDAZO[1,2-a]BENZIMIDAZOLE
2-TERT-BUTYL-1-(2-PIPERIDINOETHYL)-IMIDAZO [1,2-a]BENZIMIDAZOLE
2-TERT-BUTYL-1-(2-N,N-DIETHYLAMINOETHYL)-IMIDAZO[1,2-a]BENZIMIDAZOLE
10-(2-DIETHYLAMINOETHYL)-2,3,4,10-TETRAHYDROPYRIMIDINO[1,2-a]BENZIMIDAZOLE
10-PHENACYL-2,3,4,10-TETRAHYDROPYRIMIDINO [1,2-a]BENZIMIDAZOLE
10-(4'-CHLOROPHENACYL)-2,3,4,10-TETRAHYDROPYRIMIDINO[1,2-a]BENZIMIDAZOLE
10-(4'-METHOXYPHENACYL)-2,3,4,10-TETRAHYDROPYRIMIDINO[1,2-a]BENZIMIDAZOLE
10-[2-HYDROXY-2-(4-CHLOROPHENYL)ETHYL]-2,3,4,10-TETRAHYDROPYRIMIDINO[1,2-a]BENZIMIDAZOLE
10-[2-HYDROXY-2-(4-METHOXYPHENYL)ETHYL]-2,3,4,10-TETRAHYDROPYRIMIDINO[1,2-a]BENZIMIDAZOLE
1-(2-DIETHYLAMINOETHYL)-1,2,3,4-TETRAHYDROPYRIMIDINO[1,2-a]BENZIMIDAZOLE
1-(2-PIPERIDINOETHYL)-1,2,3,4-TETRAHYDROPYRIMIDINO[1,2-a]BENZIMIDAZOLE
1-(2-MORPHOLINOETHYL)-1,2,3,4-TETRAHYDROPYRIMIDINO[1,2-a]BENZIMIDAZOLE and
9-[2-HYDROXY-2-(4-METHOXYPHENYL)ETHYL ]-2,3-DIHYDROIMIDAZO[1,2-a]BENZIMIDAZOLE
their stereoisomers, and also their addition salts with a pharmaceutically-acceptable acid.

10. A pharmaceutical composition containing as active ingredient at least one compound according to any one of claims 1 through 9 in combination with one or more pharmaceutically-acceptable excipients or carriers.

11. A pharmaceutical composition according to claim 10 which is useful in the treatment of diabetes and/or its cardiovascular complications.

12. A method for treating a mammal afflicted with diabetes or its cardiovascular complications comprising the step of administering to the mammal an amount of a compound of any of claims 1 through 9 which is effective for alleviation of said condition.

* * * * *

UNITED STATES PATENT AND TRADEMARK OFFICE
CERTIFICATE OF CORRECTION

PATENT NO. : 5,623,073
DATED : April 22, 1997
INVENTOR(S) : V.A. Anisimova, M.V. Levchenko, T.B. Korochina, A.A. Spasov, S.G. Kovalev, G. P. Dudchenko It is certified that error appears in the above-indentified patent and that said Letters Patent is hereby corrected as shown below:

Column 12, line 59: Delete the "-" (dash) at the end of the line and Insert -- ) --.

Column 12, line 60: Delete the ")" at the beginning of the line.

Column 15, line 59: "vCH" at end of the line should read -- vOH --.

Column 16, line 63: Delete the "-" (dash) at the end of the line and Insert -- ) --.

Column 16, line 64: Delete the ")" at the beginning of the line.

Column 35, line 33: "quintuplet, H," should read -- quintuplet, 2H, --.

Column 35, line 34: "quadruplet, H," should read -- quadruplet, 4H, --.

Column 37, line 44: "10-4M" should read -- $10^{-4}M$ --.

Column 38, line 51: Insert --,-- (comma) after "aryl-lower alkyl.

UNITED STATES PATENT AND TRADEMARK OFFICE
CERTIFICATE OF CORRECTION

PATENT NO. : 5,623,073
DATED : April 22, 1997
INVENTOR(S) : V.A. Anisimova, M.V. Levchenko, T.B. Korochina, A.A. Spasov, S.G. Kovalev, G. P. Dudchenko It is certified that error appears in the above-indentified patent and that said Letters Patent is hereby corrected as shown below:

Column 38, line 57: Delete "group".

Column 38, line 66: Insert a -- , -- (comma) after the word "heteroaryl" and delete "group,"

Column 38, line 67: Delete the word "group".

Column 39, line 17: Insert a -- , -- (comma) after the word "trifluoromethyl".

Column 40, line 36: Insert a -- , -- (comma) after the word "inclusive".

Column 40, line 51: "Compound" should read -- A compound --.

UNITED STATES PATENT AND TRADEMARK OFFICE
CERTIFICATE OF CORRECTION

PATENT NO. : 5,623,073
DATED : April 22, 1997
INVENTOR(S) : V.A. Anisimova, M.V. Levchenko, T.B. Korochina, A.A. Spasov, S.G. Kovalev, G. P. Dudchenko It is certified that error appears in the above-indentified patent and that said Letters Patent is hereby corrected as shown below:

Column 40, line 56:   Insert -- form a bond -- after "X and $R_2$".

Column 40, line 58:   Delete "form a bond" after the word "acid".

Signed and Sealed this

Twenty-ninth Day of July, 1997

Attest:

BRUCE LEHMAN

Attesting Officer        Commissioner of Patents and Trademarks